United States Patent
Chidyausiku et al.

(10) Patent No.: US 11,802,141 B2
(45) Date of Patent: Oct. 31, 2023

(54) DE NOVO DESIGNED NON-LOCAL BETA SHEET PROTEINS

(71) Applicant: UNIVERSITY OF WASHINGTON, Seattle, WA (US)

(72) Inventors: Tamuka Chidyausiku, Seattle, WA (US); Enrique Marcos, Seattle, WA (US); Lucas Nivon, Seattle, WA (US); Gustav Oberdorfer, Seattle, WA (US); David Baker, Seattle, WA (US); Lauren Carter, Seattle, WA (US)

(73) Assignee: UNIVERSITY OF WASHINGTON, Seattle, WA (US)

( * ) Notice: Subject to any disclaimer, the term of this patent is extended or adjusted under 35 U.S.C. 154(b) by 295 days.

(21) Appl. No.: 17/078,319

(22) Filed: Oct. 23, 2020

(65) Prior Publication Data

US 2021/0122793 A1  Apr. 29, 2021

Related U.S. Application Data

(60) Provisional application No. 62/926,203, filed on Oct. 25, 2019.

(51) Int. Cl.
*C07K 14/47* (2006.01)
*C12N 15/11* (2006.01)
*C07K 17/00* (2006.01)

(52) U.S. Cl.
CPC .............. *C07K 14/47* (2013.01); *C07K 17/00* (2013.01); *C12N 15/111* (2013.01)

(58) Field of Classification Search
None
See application file for complete search history.

(56) References Cited

U.S. PATENT DOCUMENTS

| | | | |
|---|---|---|---|
| 7,379,822 | B2 | 5/2008 | Dahiyat et al. |
| 8,592,144 | B2 | 11/2013 | Fiedler et al. |
| 2017/0206308 | A1 | 7/2017 | Fleishman et al. |

OTHER PUBLICATIONS

Shen, Yang, and Ad Bax. "Protein backbone and sidechain torsion angles predicted from NMR chemical shifts using artificial neural networks." Journal of biomolecular NMR 56, No. 3 (2013): 227-241.
Studier, F. William. "Protein production by auto-induction in high-density shaking cultures." Protein expression and purification 41, No. 1 (2005): 207-234.
Voet, Arnout RD, Hiroki Noguchi, Christine Addy, David Simoncini, Daiki Terada, Satoru Unzai, Sam-Yong Park, Kam YJ Zhang, and Jeremy RH Tame. "Computational design of a self-assembling symmetrical β-propeller protein." Proceedings of the National Academy of Sciences 111, No. 42 (2014): 15102-15107.
Wang, Guoli, and Roland L. Dunbrack Jr. "PISCES: a protein sequence culling server." Bioinformatics 19, No. 12 (2003): 1589-1591.
King, Jinfa, Frank Delaglio, Dennis A. Torchia, and Ad Bax. "Sparse multidimensional iterative lineshape-enhanced (SMILE) reconstruction of both non-uniformly sampled and conventional NMR data." Journal of biomolecular NMR 68, No. 2 (2017): 101-118.
Zimmermann, Lukas, Andrew Stephens, Seung-Zin Nam, David Rau, Jonas Kübler, Marko Lozajic, Felix Gabler, Johannes Söding, Andrei N. Lupas, and Vikram Alva. "A completely reimplemented MPI bioinformatics toolkit with a new HHpred server at its core." Journal of molecular biology 430, No. 15 (2018): 2237-2243.
Alford, Rebecca F., Andrew Leaver-Fay, Jeliazko R. Jeliazkov, Matthew J. O'Meara, Frank P. DiMaio, Hahnbeom Park, Maxim V. Shapovalov et al. "The Rosetta all-atom energy function for macromolecular modeling and design." Journal of chemical theory and computation 13, No. 6 (2017): 3031-3048.
Altschul, Stephen F., Thomas L. Madden, Alejandro A. Schaffer, Jinghui Zhang, Zheng Zhang, Webb Miller, and David J. Lipman. "Gapped BLAST and PSI-BLAST: a new generation of protein database search programs." Nucleic acids research 25, No. 17 (1997): 3389-3402.
Berjanskii, Mark V., and David S. Wishart. "Unraveling the meaning of chemical shifts in protein NMR." Biochimica et Biophysica Acta (BBA)-Proteins and Proteomics 1865, No. 11 (2017): 1564-1576.
Bhardwaj, Gaurav, Vikram Khipple Mulligan, Christopher D. Bahl, Jason M. Gilmore, Peta J. Harvey, Olivier Cheneval, Garry W. Buchko et al. "Accurate de novo design of hyperstable constrained peptides." Nature 538, No. 7625 (2016): 329-335.
Bradley, Philip, and David Baker. "Improved beta-protein structure prediction by multilevel optimization of nonlocal strand pairings and local backbone conformation." Proteins: Structure, Function, and Bioinformatics 65, No. 4 (2006): 922-929.
Bradley, Philip, Kira MS Misura, and David Baker. "Toward high-resolution de novo structure prediction for small proteins." Science 309, No. 5742 (2005): 1868-1871.
Camacho, Christiam, George Coulouris, Vahram Avagyan, Ning Ma, Jason Papadopoulos, Kevin Bealer, and Thomas L. Madden. "BLAST+: architecture and applications." BMC bioinformatics 10, No. 1 (2009): 1-9.
Chen, Vincent B., W. Bryan Arendall, Jeffrey J. Headd, Daniel A. Keedy, Robert M. Immormino, Gary J. Kapral, Laura W. Murray, Jane S. Richardson, and David C. Richardson. "MolProbity: all-atom structure validation for macromolecular crystallography." Acta Crystallographica Section D: Biological Crystallography 66, No. 1 (2010): 12-21.
Clark, Patricia L. "Protein folding in the cell: reshaping the folding funnel." Trends in biochemical sciences 29, No. 10 (2004): 527-534.
Costantini, Susan, Giovanni Colonna, and Angelo M. Facchiano. "ESBRI: a web server for evaluating salt bridges in proteins." Bioinformation 3, No. 3 (2008): 137.

(Continued)

*Primary Examiner* — Anand U Desai
(74) *Attorney, Agent, or Firm* — MCDONNELL BOEHNEN HULBERT & BERGHOFF LLP

(57) ABSTRACT

Beta-sheet forming polypeptides at least 50%, 55%, 60%, 65%, 70%, 75%, 80%, 85%, 90%, 91%, 92%, 93%, 94%, 95%, 96%, 97%, 98%, 99%, or 100% identical to the amino acid sequence selected from the group consisting of SEQ ID NOS:1-24 are disclosed, together with their use and methods for designing beta-sheet forming polypeptides.

11 Claims, 10 Drawing Sheets

Specification includes a Sequence Listing.

(56) References Cited

OTHER PUBLICATIONS

Delaglio, Frank, Stephan Grzesiek, Geerten W. Vuister, Guang Zhu, John Pfeifer, and A. D. Bax. "NMRPipe: a multidimensional spectral processing system based on UNIX pipes." Journal of biomolecular NMR 6, No. 3 (1995): 277-293.
Dou, Jiayi, Anastassia A. Vorobieva, William Sheffler, Lindsey A. Doyle, Hahnbeom Park, Matthew J. Bick, Binchen Miao et al. "De novo design of a fluorescence-activating β-barrel." Nature 561, No. 7724 (2018): 485-491.
Evangelidis, Thomas, Santrupti Nerli, Jiří Nováček, Andrew E. Brereton, P. Andrew Karplus, Rochelle R. Dotas, Vincenzo Venditti, Nikolaos G. Sgourakis, and Konstantinos Tripsianes. "Automated NMR resonance assignments and structure determination using a minimal set of 4D spectra." Nature communications 9, No. 1 (2018): 1-13.
Fleishman, Sarel J., Andrew Leaver-Fay, Jacob E. Corn, Eva-Maria Strauch, Sagar D. Khare, Nobuyasu Koga, Justin Ashworth et al. "RosettaScripts: a scripting language interface to the Rosetta macromolecular modeling suite." PloS one 6, No. 6 (2011): e20161.
Hecht, Michael H. "De novo design of beta-sheet proteins." Proceedings of the National Academy of Sciences of the United States of America 91, No. 19 (1994): 8729.
Hennetin, Jérôme, Bérangère Jullian, Alasdair C. Steven, and Andrey V. Kajava. "Standard conformations of β-arches in β-solenoid proteins." Journal of molecular biology 358, No. 4 (2006): 1094-1105.
Herrmann, Torsten, Peter Güntert, and Kurt Wüthrich. "Protein NMR structure determination with automated NOE assignment using the new software CANDID and the torsion angle dynamics algorithm DYANA." Journal of molecular biology 319, No. 1 (2002): 209-227.
Holm, Liisa, and Laura M. Laakso. "Dali server update." Nucleic acids research 44, No. W1 (2016): W351-W355.
Hu, Xiaozhen, Huanchen Wang, Hengming Ke, and Brian Kuhlman. "Computer-based redesign of a β sandwich protein suggests that extensive negative design is not required for de novo β sheet design." Structure 16, No. 12 (2008): 1799-1805.
Hughes, Robert M., and Marcey L. Waters. "Model systems for β-hairpins and β-sheets." Current opinion in structural biology 16, No. 4 (2006): 514-524.
Jones, David T. "Protein secondary structure prediction based on position-specific scoring matrices." Journal of molecular biology 292, No. 2 (1999): 195-202.
Kabsch, Wolfgang, and Christian Sander. "Dictionary of protein secondary structure: pattern recognition of hydrogen-bonded and geometrical features." Biopolymers: Original Research on Biomolecules 22, No. 12 (1983): 2577-2637.
Kajava, Andrey V., Ulrich Baxa, and Alasdair C. Steven. "β arcades: recurring motifs in naturally occurring and disease-related amyloid fibrils." The FASEB journal 24, No. 5 (2010): 1311-1319.
King, Indigo Chris, James Gleixner, Lindsey Doyle, Alexandre Kuzin, John F. Hunt, Rong Xiao, Gaetano T. Montelione, Barry L. Stoddard, Frank DiMaio, and David Baker. "Precise assembly of complex beta sheet topologies from de novo designed building blocks." Elife 4 (2015): e11012.
Koga, Nobuyasu, Rie Tatsumi-Koga, Gaohua Liu, Rong Xiao, Thomas B. Acton, Gaetano T. Montelione, and David Baker. "Principles for designing ideal protein structures." Nature 491, No. 7423 (2012): 222-227.
Kortemme, Tanja, Marina Ramírez-Alvarado, and Luis Serrano. "Design of a 20-amino acid, three-stranded β-sheet protein." Science 281, No. 5374 (1998): 253-256.
Kuhlman, Brian, Gautam Dantas, Gregory C. Ireton, Gabriele Varani, Barry L. Stoddard, and David Baker. "Design of a novel globular protein fold with atomic-level accuracy." science 302, No. 5649 (2003): 1364-1368.
Kuhlman, Brian, and David Baker. "Native protein sequences are close to optimal for their structures." Proceedings of the National Academy of Sciences 97, No. 19 (2000): 10383-10388.
Kuhn, Michael, Jens Meiler, and David Baker. "Strand-loop-strand motifs: prediction of hairpins and diverging turns in proteins." Proteins: Structure, Function, and Bioinformatics 54, No. 2 (2004): 282-288.
Lange, Oliver F., and David Baker. "Resolution-adapted recombination of structural features significantly improves sampling in restraint-guided structure calculation." Proteins: Structure, Function, and Bioinformatics 80, No. 3 (2012): 884-895.
Lange, Oliver F. "Automatic NOESY assignment in CS-RASREC-Rosetta." Journal of biomolecular NMR 59, No. 3 (2014): 147-159.
Lee, Woonghee, Marco Tonelli, and John L. Markley. "NMRFAM-SPARKY: enhanced software for biomolecular NMR spectroscopy." Bioinformatics 31, No. 8 (2015): 1325-1327.
Lin, Yu-Ru, Nobuyasu Koga, Rie Tatsumi-Koga, Gaohua Liu, Amanda F. Clouser, Gaetano T. Montelione, and David Baker. "Control over overall shape and size in de novo designed proteins." Proceedings of the National Academy of Sciences 112, No. 40 (2015): E5478-E5485.
MacDonald, James T., Burak V. Kabasakal, David Godding, Sebastian Kraatz, Louie Henderson, James Barber, Paul S. Freemont, and James W. Murray. "Synthetic beta-solenoid proteins with the fragment-free computational design of a beta-hairpin extension." Proceedings of the National Academy of Sciences 113, No. 37 (2016): 10346-10351.
Marcos, Enrique, and Daniel-Adriano Silva. "Essentials of de novo protein design: Methods and applications." Wiley Interdisciplinary Reviews: Computational Molecular Science 8, No. 6 (2018): e1374.
Marcos, Enrique, Benjamin Basanta, Tamuka M. Chidyausiku, Yuefeng Tang, Gustav Oberdorfer, Gaohua Liu, G. V. T. Swapna et al. "Principles for designing proteins with cavities formed by curved β sheets." Science 355, No. 6321 (2017): 201-206.
Nanda, Vikas, Michael M. Rosenblatt, Artur Osyczka, Hidetoshi Kono, Zelleka Getahun, P. Leslie Dutton, Jeffery G. Saven, and William F. DeGrado. "De novo design of a redox-active minimal rubredoxin mimic." Journal of the American Chemical Society 127, No. 16 (2005): 5804-5805.
Nerli, Santrupti, Andrew C. McShan, and Nikolaos G. Sgourakis. "Chemical shift-based methods in NMR structure determination." Progress in nuclear magnetic resonance spectroscopy 106 (2018): 1-25.
Nilges, Michael. "Ambiguous distance data in the calculation of NMR structures." Folding and Design 2 (1997): S53-S57.
Nilges, Michael. "A calculation strategy for the structure determination of symmetric demers by 1H NMR." Proteins: Structure, Function, and Bioinformatics 17, No. 3 (1993): 297-309.
Noguchi, Hiroki, Christine Addy, David Simoncini, Staf Wouters, Bram Mylemans, Luc Van Meervelt, Thomas Schiex, Kam YJ Zhang, Jeremy RH Tame, and Arnout RD Voet. "Computational design of symmetrical eight-bladed β-propeller proteins." IUCrJ 6, No. 1 (2019): 46-55.
O'Meara, Matthew J., Andrew Leaver-Fay, Michael D. Tyka, Amelie Stein, Kevin Houlihan, Frank DiMaio, Philip Bradley et al. "Combined covalent-electrostatic model of hydrogen bonding improves structure prediction with Rosetta." Journal of chemical theory and computation 11, No. 2 (2015): 609-622.
Ottesen, Jennifer J., and Barbara Imperiali. "Design of a discretely folded mini-protein motif with predominantly β-structure." nature structural biology 8, No. 6 (2001): 535-539.
Plaxco, Kevin W., Kim T. Simons, and David Baker. "Contact order, transition state placement and the refolding rates of single domain proteins." Journal of molecular biology 277, No. 4 (1998): 985-994.
The PyMOL Molecular Graphics System, Version 2.0 Schrödinger, LLC.
Quinn, Thomas P., Neil B. Tweedy, Robert W. Williams, Jane S. Richardson, and David C. Richardson. "Betadoublet: de novo design, synthesis, and characterization of a beta-sandwich protein." Proceedings of the National Academy of Sciences 91, No. 19 (1994): 8747-8751.

(56) References Cited

OTHER PUBLICATIONS

Richardson, Jane S., and David C. Richardson. "Natural β-sheet proteins use negative design to avoid edge-to-edge aggregation." Proceedings of the National Academy of Sciences 99, No. 5 (2002): 2754-2759.
Rohl, Carol A., Charlie EM Strauss, Kira MS Misura, and David Baker. "Protein structure prediction using Rosetta." Methods in enzymology 383 (2004): 66-93.
Searle, Mark S., and Barbara Ciani. "Design of β-sheet systems for understanding the thermodynamics and kinetics of protein folding." Current opinion in structural biology 14, No. 4 (2004): 458-464.
Sheffler, William, and David Baker. "RosettaHoles2: a volumetric packing measure for protein structure refinement and validation." Protein Science 19, No. 10 (2010): 1991-1995.

6A

6B

6C

9A

9B

SEQUENCE LISTING

<160> NUMBER OF SEQ ID NOS: 24

<210> SEQ ID NO 1
<211> LENGTH: 70
<212> TYPE: PRT
<213> ORGANISM: Artificial Sequence
<220> FEATURE:
<223> OTHER INFORMATION: Synthetic peptide

<400> SEQUENCE: 1

Pro Glu Thr Lys Thr Tyr Arg Phe Thr Pro Gly Glu Arg Glu Tyr
1               5                   10                  15

Glu Phe Asn Thr Asp Val Glu Val Glu Val Asn His Asp Met Glu Ile
            20                  25                  30

Thr Val Asn Gly Gln Thr Gln Arg Tyr Thr Pro Gly Thr Ser Val Arg
        35                  40                  45

Val Pro Pro Gly Ser Arg Val Arg Ile Arg Val Asn Asp Asp Val Lys
    50                  55                  60

Val Asn Trp His Glu Arg
65                  70

<210> SEQ ID NO 2
<211> LENGTH: 74
<212> TYPE: PRT
<213> ORGANISM: Artificial Sequence
<220> FEATURE:
<223> OTHER INFORMATION: Synthetic peptide

<400> SEQUENCE: 2

Gln His Thr Arg Thr Tyr Arg Leu Thr Pro Gly Glu Gln Glu Phe
1               5                   10                  15

Lys Tyr Asn Thr Pro Met Thr Met His Val Glu Val Asn Thr Asp Val
            20                  25                  30

Glu Ile Glu Tyr Asn Gly Lys Gly Gln Arg Tyr Pro Pro Gly Thr Glu
        35                  40                  45

Val Glu Ile Glu Val Arg Pro Gly Thr Lys Val Arg Ile Lys Val Asn
    50                  55                  60

Thr Asp Val Arg Val Glu Ile Arg Glu Asn
65                  70

<210> SEQ ID NO 3
<211> LENGTH: 70
<212> TYPE: PRT
<213> ORGANISM: Artificial Sequence
<220> FEATURE:
<223> OTHER INFORMATION: Synthetic peptide

<400> SEQUENCE: 3

Pro Glu Thr Arg Thr Tyr Arg Phe Thr Pro Gly Glu Arg Glu Phe
1               5                   10                  15

Glu Phe Asp Thr Asn Val Glu Phe Arg Phe Asp Ser Asp Val Glu Val
            20                  25                  30

Thr Val Asn Gly Gln Thr Thr Arg Val Pro Pro Gly Ser Ser Val Glu
        35                  40                  45

Val Pro Pro Gly Ser Arg Ile Arg Ile Arg Val Asn Thr Asp Leu Gln
    50                  55                  60

Val Glu Val Arg Arg Arg
65                  70

<210> SEQ ID NO 4

```
<211> LENGTH: 70
<212> TYPE: PRT
<213> ORGANISM: Artificial Sequence
<220> FEATURE:
<223> OTHER INFORMATION: Synthetic peptide

<400> SEQUENCE: 4

Pro Glu Thr Arg Thr Tyr Arg Phe Thr Pro Gly Glu Glu Arg Glu Phe
1               5                   10                  15

Glu His Asp Thr Asn Val Lys Trp Lys Phe Asn Thr Asp Val Glu Ile
            20                  25                  30

Glu Arg Asn Gly Glu Arg Thr Arg Phe Thr Pro Gly Glu Glu Val Glu
        35                  40                  45

Val Pro Pro Gly Thr Arg Val Arg Ile Arg Val Asn Thr Asp Val Gln
    50                  55                  60

Phe Thr Leu Glu Arg Asn
65                  70

<210> SEQ ID NO 5
<211> LENGTH: 70
<212> TYPE: PRT
<213> ORGANISM: Artificial Sequence
<220> FEATURE:
<223> OTHER INFORMATION: Synthetic peptide

<400> SEQUENCE: 5

Pro Glu Arg Arg Glu Ile Arg Leu Ser Pro Gly Glu Arg Tyr Thr Phe
1               5                   10                  15

Thr Val Asp Thr Asp Val Gln Phe Arg Val Glu Lys Pro Val Arg Val
            20                  25                  30

Arg His Asp Gly Thr Glu Thr Glu Tyr Lys Pro Gly Thr His Leu Arg
        35                  40                  45

Leu Pro Pro Gly Thr Ser Val Thr Phe Glu Val Asp Thr Asp Val Arg
    50                  55                  60

Phe Glu Ile Gln Arg Asn
65                  70

<210> SEQ ID NO 6
<211> LENGTH: 70
<212> TYPE: PRT
<213> ORGANISM: Artificial Sequence
<220> FEATURE:
<223> OTHER INFORMATION: Synthetic peptide

<400> SEQUENCE: 6

Pro Glu Arg Arg Glu Ile Arg Leu Ser Pro Gly Glu Arg Tyr Thr Phe
1               5                   10                  15

Thr Val Asp Thr Pro Val Gln Phe Arg Val Glu Lys Pro Val Arg Val
            20                  25                  30

Arg Tyr Asp Gly Thr Glu Thr Glu Leu Lys Pro Gly Ser His Leu Arg
        35                  40                  45

Leu Pro Pro Gly Thr Ser Ile Thr Phe Glu Val Asp Thr Pro Val Arg
    50                  55                  60

Phe Glu Ile Gln Arg Asn
65                  70

<210> SEQ ID NO 7
<211> LENGTH: 68
<212> TYPE: PRT
<213> ORGANISM: Artificial Sequence
<220> FEATURE:
```

<223> OTHER INFORMATION: Synthetic peptide

<400> SEQUENCE: 7

Ser Arg Tyr Glu Ile Thr Gly Asn Pro Gly Thr Arg Val Glu Leu Arg
1               5                   10                  15

Glu Asn Pro Gly Ser Arg Val Lys Ser Asn Ala Pro Gly Arg Ser Glu
            20                  25                  30

Arg Asn Gly Glu His Arg Thr Trp Asn Pro Gly Glu Ser Arg Thr Ser
        35                  40                  45

Asn Arg Pro Ser Thr Met Glu Val Glu Ser Asp Gly Pro Ile Ser Ile
    50                  55                  60

Glu Ile Arg Glu
65

<210> SEQ ID NO 8
<211> LENGTH: 68
<212> TYPE: PRT
<213> ORGANISM: Artificial Sequence
<220> FEATURE:
<223> OTHER INFORMATION: Synthetic peptide

<400> SEQUENCE: 8

Glu Ser Lys Lys Ile Thr Val Asn Ala Gly Glu Arg Met Thr Leu His
1               5                   10                  15

Leu Asn Ala Gly Thr Glu Val Arg Ser Glu Pro Gly Arg Glu His
            20                  25                  30

Ser Asn Gly Gln Thr Gln Gln Trp Pro Pro Gly Ser Thr Ile Arg Ser
        35                  40                  45

Asp Gln Pro Thr Thr Thr Thr Phe Glu Ser Asp Arg Pro Leu Thr Leu
    50                  55                  60

Glu Val Arg Gln
65

<210> SEQ ID NO 9
<211> LENGTH: 68
<212> TYPE: PRT
<213> ORGANISM: Artificial Sequence
<220> FEATURE:
<223> OTHER INFORMATION: Synthetic peptide

<400> SEQUENCE: 9

Lys Thr Lys Thr Tyr Thr Val Asn Pro Gly Glu Lys Val Thr Ile Thr
1               5                   10                  15

Met Asn Pro Gly Asp Glu Met Thr Ala Glu Gly Pro Val Thr Ser Arg
            20                  25                  30

Ala Arg Gly Gln Glu Gln Thr Val Asn Pro Gly Glu Thr Val Arg Val
        35                  40                  45

Asn Glu Pro Gly Thr Phe Thr Leu Glu Ser Asp Arg Pro Val Thr Val
    50                  55                  60

Lys Ile Gln His
65

<210> SEQ ID NO 10
<211> LENGTH: 78
<212> TYPE: PRT
<213> ORGANISM: Artificial Sequence
<220> FEATURE:
<223> OTHER INFORMATION: Synthetic peptide

<400> SEQUENCE: 10

```
Thr Arg Glu Thr Lys Val Thr Val Asn Pro Gly Glu Glu Tyr Glu Val
1               5                   10                  15

Lys Val Asn Pro Gly Thr Arg Val Glu Ile Gln Ala Lys Gly Pro Ala
                20                  25                  30

Glu Phe Glu Gly Gly Gly Thr Arg Thr Arg Leu Asn Pro Gly Glu Ser
            35                  40                  45

Tyr Lys Phe Glu Asn Leu Thr Ser Gln Pro Leu Arg Ile Arg Leu Arg
50                  55                  60

Asn Leu Ser Asp Thr Pro Ile Glu Phe Arg Ile Arg Glu Glu
65                  70                  75
```

<210> SEQ ID NO 11
<211> LENGTH: 82
<212> TYPE: PRT
<213> ORGANISM: Artificial Sequence
<220> FEATURE:
<223> OTHER INFORMATION: Synthetic peptide

<400> SEQUENCE: 11

```
Ser Glu Arg Arg Glu Tyr Glu Val Asn Pro Gly Glu Arg Met Glu Phe
1               5                   10                  15

Thr Ile Asn Lys Gly Glu Arg Phe Glu Phe Lys Thr Asn Arg Pro Met
                20                  25                  30

Thr Val Arg Val Glu Leu Asp Gly Arg Glu Glu Arg Tyr Thr Ala Thr
            35                  40                  45

Pro Gly Glu Ser Ile Ser Val Gln Asn Asn Ser Asp Asn Pro Ala Arg
50                  55                  60

Val Glu Ile Gln Asn Asp Ser Asp Glu Pro Val Arg Val Glu Val Arg
65                  70                  75                  80

Arg His
```

<210> SEQ ID NO 12
<211> LENGTH: 94
<212> TYPE: PRT
<213> ORGANISM: Artificial Sequence
<220> FEATURE:
<223> OTHER INFORMATION: Synthetic peptide

<400> SEQUENCE: 12

```
Pro Ile Asp Val Arg Ile Arg Met Pro Pro Gly Ser Thr Phe Arg Val
1               5                   10                  15

Thr Ile Lys Thr Asp Val Glu Val Gln Val Asn Lys Pro Val Arg Val
                20                  25                  30

Glu His Asp Gly Thr Arg Thr Glu Tyr Lys Pro Gly Thr His Leu Arg
            35                  40                  45

Ile Pro Pro Gly Ser Glu Val Arg Phe Glu Val Asp Thr Asp Val Glu
50                  55                  60

Phe Arg Phe Lys Val Thr Asp Pro Glu Thr Val Lys Glu Met Glu Glu
65                  70                  75                  80

His Ala Arg Glu His Gly Leu Glu Tyr Glu Thr Arg Ser Asp
                85                  90
```

<210> SEQ ID NO 13
<211> LENGTH: 70
<212> TYPE: PRT
<213> ORGANISM: Artificial Sequence
<220> FEATURE:
<223> OTHER INFORMATION: Synthetic peptide

<400> SEQUENCE: 13

```
Pro Glu Arg Arg Cys Ile Arg Leu Ser Pro Gly Arg Tyr Thr Phe
1               5                   10                  15

Thr Val Asp Thr Pro Val Cys Phe Arg Val Glu Lys Pro Val Arg Val
                20                  25                  30

Arg Tyr Asp Gly Thr Glu Thr Glu Leu Lys Pro Gly Ser His Leu Cys
            35                  40                  45

Leu Pro Pro Gly Thr Ser Ile Thr Phe Glu Val Asp Thr Pro Val Arg
        50                  55                  60

Phe Cys Ile Gln Arg Asn
65                  70
```

<210> SEQ ID NO 14
<211> LENGTH: 70
<212> TYPE: PRT
<213> ORGANISM: Artificial Sequence
<220> FEATURE:
<223> OTHER INFORMATION: Synthetic peptide

<400> SEQUENCE: 14

```
Pro Glu Arg Arg Glu Ile Cys Leu Ser Pro Gly Arg Tyr Thr Phe
1               5                   10                  15

Thr Val Asp Thr Pro Val Gln Phe Arg Val Glu Lys Pro Val Arg Val
                20                  25                  30

Arg Tyr Asp Gly Thr Glu Thr Glu Leu Lys Pro Gly Ser His Leu Arg
            35                  40                  45

Leu Pro Pro Gly Thr Ser Ile Thr Phe Glu Val Asp Thr Pro Val Cys
        50                  55                  60

Phe Glu Ile Gln Arg Asn
65                  70
```

<210> SEQ ID NO 15
<211> LENGTH: 70
<212> TYPE: PRT
<213> ORGANISM: Artificial Sequence
<220> FEATURE:
<223> OTHER INFORMATION: Synthetic peptide

<400> SEQUENCE: 15

```
Pro Glu Arg Arg Glu Ile Arg Leu Ser Pro Gly Arg Tyr Thr Phe
1               5                   10                  15

Thr Val Asp Thr Pro Val Gln Phe Cys Val Glu Lys Pro Val Arg Val
                20                  25                  30

Arg Tyr Asp Gly Thr Glu Thr Glu Leu Lys Pro Gly Ser Cys Leu Arg
            35                  40                  45

Leu Pro Pro Gly Thr Ser Ile Thr Phe Glu Val Asp Thr Pro Val Arg
        50                  55                  60

Phe Glu Ile Gln Arg Asn
65                  70
```

<210> SEQ ID NO 16
<211> LENGTH: 94
<212> TYPE: PRT
<213> ORGANISM: Artificial Sequence
<220> FEATURE:
<223> OTHER INFORMATION: Synthetic peptide

<400> SEQUENCE: 16

```
Pro Ile Asp Val Arg Ile Cys Met Pro Pro Gly Ser Thr Phe Arg Val
1               5                   10                  15
```

```
Thr Ile Lys Thr Pro Val Glu Val Gln Val Asn Lys Pro Val Arg Val
            20                  25                  30

Glu Tyr Asp Gly Thr Arg Thr Glu Leu Lys Pro Gly Ser His Leu Arg
        35                  40                  45

Ile Pro Pro Gly Ser Glu Ile Arg Phe Glu Val Asp Thr Pro Val Cys
    50                  55                  60

Phe Arg Phe Lys Val Thr Asp Pro Glu Thr Val Lys Glu Met Glu Glu
65                  70                  75                  80

His Ala Arg Glu His Gly Leu Glu Tyr Glu Thr Arg Ser Asp
                85                  90
```

<210> SEQ ID NO 17
<211> LENGTH: 94
<212> TYPE: PRT
<213> ORGANISM: Artificial Sequence
<220> FEATURE:
<223> OTHER INFORMATION: Synthetic peptide

<400> SEQUENCE: 17

```
Pro Ile Asp Cys Arg Ile Arg Met Pro Pro Gly Ser Thr Phe Arg Val
1               5                   10                  15

Thr Ile Lys Thr Pro Val Glu Val Gln Val Asn Lys Pro Val Arg Val
            20                  25                  30

Glu Tyr Asp Gly Thr Arg Thr Glu Leu Lys Pro Gly Ser His Leu Arg
        35                  40                  45

Ile Pro Pro Gly Ser Glu Ile Arg Phe Glu Val Asp Thr Pro Val Glu
    50                  55                  60

Phe Arg Phe Lys Val Thr Asp Pro Glu Thr Val Lys Glu Met Glu Glu
65                  70                  75                  80

His Ala Arg Glu His Gly Leu Glu Tyr Glu Cys Arg Ser Asp
                85                  90
```

<210> SEQ ID NO 18
<211> LENGTH: 94
<212> TYPE: PRT
<213> ORGANISM: Artificial Sequence
<220> FEATURE:
<223> OTHER INFORMATION: Synthetic peptide

<400> SEQUENCE: 18

```
Pro Ile Asp Cys Arg Ile Arg Met Pro Pro Gly Ser Thr Phe Arg Val
1               5                   10                  15

Thr Ile Lys Thr Pro Val Glu Val Gln Val Asn Lys Pro Val Arg Val
            20                  25                  30

Glu Tyr Asp Gly Thr Arg Thr Glu Leu Lys Pro Gly Ser His Leu Arg
        35                  40                  45

Ile Pro Pro Gly Ser Glu Ile Arg Phe Glu Val Asp Thr Pro Val Glu
    50                  55                  60

Phe Arg Phe Lys Val Thr Asp Pro Glu Thr Val Lys Glu Cys Glu Glu
65                  70                  75                  80

His Ala Arg Glu His Gly Leu Glu Tyr Glu Thr Arg Ser Asp
                85                  90
```

<210> SEQ ID NO 19
<211> LENGTH: 94
<212> TYPE: PRT
<213> ORGANISM: Artificial Sequence
<220> FEATURE:
<223> OTHER INFORMATION: Synthetic peptide

<400> SEQUENCE: 19

Asn Cys Asp Val Arg Val Arg Val Pro Pro Gly Ser Glu Val Arg Leu
1               5                   10                  15

Thr Phe Lys Thr Asp Val Arg Ile Glu Val Lys Asn Pro Met Glu Val
            20                  25                  30

Arg His Asp Gly Thr Glu Thr Arg Tyr Thr Pro Gly Thr His Leu Arg
        35                  40                  45

Ile Pro Pro Gly Ser Gln Val Asp Phe Arg Val Asn Thr Asp Val Glu
    50                  55                  60

Phe His Leu Glu Met Asp Asn Pro Glu Thr Ala Lys Glu Val Glu Glu
65                  70                  75                  80

Gln Ala Arg Arg Gln Gly Val Glu Val Glu Val Arg Cys Gln
                85                  90

<210> SEQ ID NO 20
<211> LENGTH: 78
<212> TYPE: PRT
<213> ORGANISM: Artificial Sequence
<220> FEATURE:
<223> OTHER INFORMATION: Synthetic peptide

<400> SEQUENCE: 20

Thr Arg Glu Thr Lys Val Thr Val Asn Pro Gly Glu Glu Tyr Glu Val
1               5                   10                  15

Lys Val Asn Pro Gly Thr Arg Val Glu Ile Gln Ala Lys Gly Pro Ala
            20                  25                  30

Glu Phe Glu Gly Gly Gly Thr Arg Thr Arg Leu Asn Pro Gly Glu Ser
        35                  40                  45

Tyr Lys Phe Glu Asn Leu Thr Ser Gln Pro Leu Arg Lys Arg Leu Arg
    50                  55                  60

Val Leu Ser Asp Thr Pro Ile Glu Phe Arg Ile Arg Glu Glu
65                  70                  75

<210> SEQ ID NO 21
<211> LENGTH: 78
<212> TYPE: PRT
<213> ORGANISM: Artificial Sequence
<220> FEATURE:
<223> OTHER INFORMATION: Synthetic peptide

<400> SEQUENCE: 21

Thr Arg Glu Thr Lys Val Thr Val Asn Pro Gly Glu Glu Tyr Glu Val
1               5                   10                  15

Lys Val Asn Pro Gly Thr Arg Val Glu Ile Gln Ala Lys Gly Pro Ala
            20                  25                  30

Glu Phe Glu Gly Gly Gly Thr Arg Thr Arg Leu Asn Pro Gly Glu Ser
        35                  40                  45

Tyr Lys Phe Glu Asn Leu Thr Ser Gln Pro Leu Arg Ile Arg Lys Arg
    50                  55                  60

Val Leu Ser Asp Thr Pro Ile Glu Phe Arg Ile Arg Glu Glu
65                  70                  75

<210> SEQ ID NO 22
<211> LENGTH: 78
<212> TYPE: PRT
<213> ORGANISM: Artificial Sequence
<220> FEATURE:
<223> OTHER INFORMATION: Synthetic peptide

<400> SEQUENCE: 22

```
Thr Arg Glu Thr Lys Val Thr Val Asn Pro Gly Glu Tyr Glu Val
1               5                   10                  15

Lys Val Asn Pro Gly Thr Arg Val Glu Ile Gln Ala Lys Gly Pro Ala
                20                  25                  30

Glu Phe Glu Gly Gly Gly Thr Arg Thr Arg Leu Asn Pro Gly Glu Ser
            35                  40                  45

Tyr Lys Phe Glu Asn Leu Thr Ser Gln Pro Leu Arg Ile Arg Lys Arg
        50                  55                  60

Asn Leu Ser Asp Thr Pro Ile Glu Phe Arg Ile Arg Glu Glu
65                  70                  75
```

<210> SEQ ID NO 23
<211> LENGTH: 78
<212> TYPE: PRT
<213> ORGANISM: Artificial Sequence
<220> FEATURE:
<223> OTHER INFORMATION: Synthetic peptide

<400> SEQUENCE: 23

```
Thr Arg Glu Thr Lys Cys Thr Val Asn Pro Gly Glu Tyr Glu Val
1               5                   10                  15

Lys Val Asn Pro Gly Thr Arg Val Glu Ile Gln Ala Lys Gly Pro Ala
                20                  25                  30

Glu Phe Glu Gly Gly Gly Thr Arg Thr Arg Leu Asn Pro Gly Glu Ser
            35                  40                  45

Tyr Lys Phe Glu Asn Leu Thr Ser Gln Pro Leu Arg Ile Arg Leu Arg
        50                  55                  60

Asn Leu Ser Asp Thr Pro Ile Glu Phe Arg Ile Arg Glu Glu
65                  70                  75
```

<210> SEQ ID NO 24
<211> LENGTH: 78
<212> TYPE: PRT
<213> ORGANISM: Artificial Sequence
<220> FEATURE:
<223> OTHER INFORMATION: Synthetic peptide

<400> SEQUENCE: 24

```
Thr Arg Glu Thr Lys Val Thr Val Asn Pro Gly Glu Tyr Glu Val
1               5                   10                  15

Lys Val Asn Pro Gly Thr Arg Val Glu Ile Gln Ala Lys Gly Pro Ala
                20                  25                  30

Glu Phe Glu Gly Gly Gly Cys Arg Thr Arg Leu Asn Pro Gly Glu Ser
            35                  40                  45

Tyr Lys Phe Glu Asn Leu Thr Ser Gln Pro Leu Arg Ile Arg Leu Arg
        50                  55                  60

Asn Leu Ser Asp Thr Pro Ile Glu Phe Arg Ile Arg Glu Glu
65                  70                  75
```

DE NOVO DESIGNED NON-LOCAL BETA SHEET PROTEINS

CROSS REFERENCE

This application claims priority to U.S. Provisional Patent Application Ser. No. 62/926,203 filed Oct. 25, 2019, incorporated by reference herein in its entirety.

SEQUENCE LISTING STATEMENT

A computer readable form of the Sequence Listing is filed with this application by electronic submission and is incorporated into this application by reference in its entirety. The Sequence Listing is contained in the file created on Oct. 8, 2020, having the file name "19-1613-US_Sequence-Listing_ SEQ.txt" and is 18.3 kb in size.

BACKGROUND

β-sheet proteins carry out critical functions in biology, and hence are attractive scaffolds for computational protein design. Despite this potential, de novo design of all β-sheet proteins from first principles lags far behind the design of all-α or mixed αβ domains due to their non-local nature and tendency of exposed β-strand edges to aggregate.

SUMMARY

In one aspect, the disclosure provides polypeptides. comprising an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence selected from the group consisting of SEQ ID NOS:1-24, wherein the polypeptide forms a beta-sheet. In one embodiment, the polypeptide may comprise two beta-sheets packing against each other forming a double-stranded beta-helix formed by 8 antiparallel beta-strands. In another embodiment, the polypeptide may comprise an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence selected from the group consisting of SEQ ID NOS:10, 11, and 20-24. In one embodiment, amino acid changes from the reference polypeptide do not include changes in proline residues present in loop connections between beta strands. In another embodiment, amino acid changes from the reference polypeptide do not include changes in polar amino acid residues present in loop connections between beta strands capable of forming hydrogen bonds to the loop backbone. In a further embodiment, amino acid changes from the reference polypeptide do not include changes in hydrophobic amino acid residues present in the loop connections and adjacent to the polar amino acid residues between beta strands capable of forming hydrogen bonds to the loop backbone.

In one embodiment, amino acid changes from the reference polypeptide do not include changes in hydrophobic amino acid residues stabilizing the polypeptide core. In another embodiment, amino acid changes from the reference polypeptide are conservative amino acid substitutions.

In other aspects, the disclosure provides nucleic acids encoding the polypeptide of any embodiment or combination of embodiments of the disclosure; expression vectors comprising the nucleic acids of the disclosure linked to a control sequence; host cells comprising the nucleic acid and/or expression vector of the disclosure; cells expressing the polypeptide of any embodiment or combination of embodiments of the disclosure; and pharmaceutical composition comprising the polypeptide of any embodiment or combination of embodiments of the disclosure and a pharmaceutically acceptable carrier.

In another aspect, the disclosure provides methods for use of the polypeptide of any embodiment or combination of embodiments of the disclosure for any suitable purpose, including but not limited to as scaffolds for virus capsids and antibodies and to transport hydrophobic molecules, for use in recognition and enzymatic processing of carbohydrates; incorporating metal, ligand-binding and active sites.

In another aspect, the disclosure provides methods for designing polypeptides that form a double-stranded β-helix formed by 8 antiparallel β-strands, comprising the steps of any embodiment or combinations of embodiments disclosed herein.

DETAILED DESCRIPTION

Figure 1:
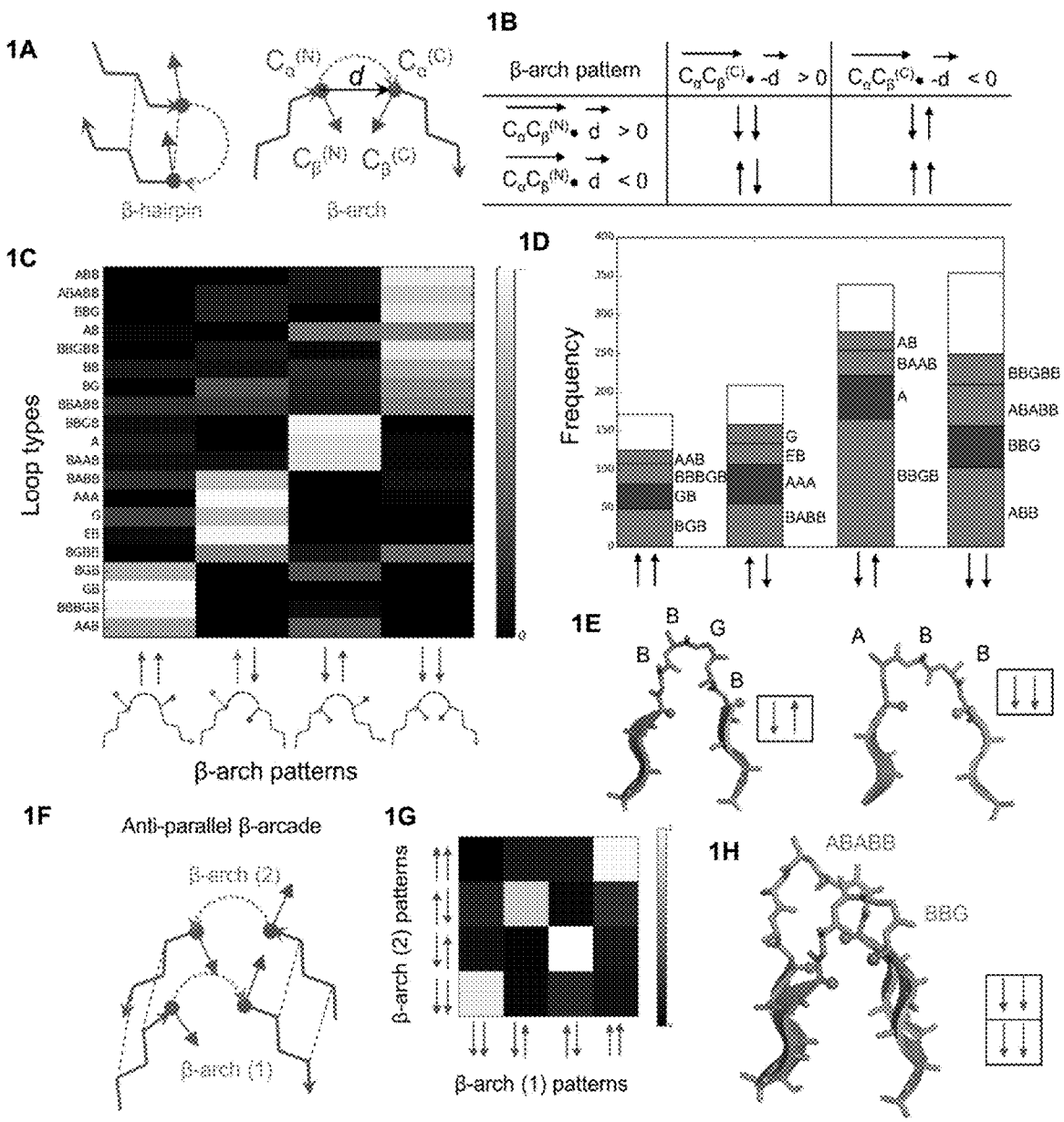
FIG. 1A-1H. Constraints on β-arch geometry. (A) Sidechain directionality in the β-arch. (B) comparison between β-hairpin and β-arch; the CαCβ and d vectors used to define the orientation of the two adjacent sidechains are indicated. The four possible sidechain directionality patterns are on the right. (C) Turn type dependence of β-arch sidechain patterns. Loops on the y-axis are described by their ABEGO torsion bins (FIG. 4). Most of the loops adopt only one of the four possible sidechain patterns. (D) Frequency of the most common loops for each of the four β-arch sidechain patterns. There are strong preferences, for example BBGB is strongly associated with the "↓↑" pattern, whereas ABB is strongly associated with the "↓↓" pattern (E). Only loops with bending <120 degrees (Methods) and containing between 1 and 5 amino acids were considered in this analysis. (F) Two stacked β-arches having in-register strand pairing form β-arcades. (G) Since strand pairs of the β-arcade are in-register, the sidechains adjacent to one β-arch loop must have the same orientation as the paired sidechains that are adjacent to the second β-arch loop, and therefore not all loop pairs are allowed. (H) Example of a β-arcade formed by two common β-arches with compatible sidechain patterns.

As used herein, the amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

All references cited are herein incorporated by reference in their entirety. Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*, 2$^{nd}$ Ed. (R. I. Freshney. 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog (Ambion, Austin, Tex.).

As used herein, the singular forms "a", "an" and "the" include plural referents unless the context clearly dictates otherwise.

All embodiments of any aspect of the disclosure can be used in combination, unless the context clearly dictates otherwise.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

In one aspect, the disclosure provides polypeptide comprising an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence selected from the group consisting of SEQ ID NOS:1-24, wherein the polypeptide forms a beta-sheet. As disclosed in the attached appendices, the inventors have provided the first accurate de novo design of beta-sheet polypeptides with the jelly roll fold. Beta-strand positions are shown in Table 1 in bold and underlined font, with non-highlighted residue between the beta strands are loop connections between the beta strands.

Such beta-sheet polypeptides can be used, for example, as protein scaffolds for metal, ligand-binding or enzyme active sites. The ability to design these "de novo" allows tailoring their structure for target recognition sites with both high structural accuracy and thermostability.

TABLE 1

| Design name | Amino acid sequence |
|---|---|
| BH_1<br>SEQ ID NO: 1 | PETKTYRFTPGEEREYEENTDVEVEVNHDMEITVNGQTQRYTPGTSV<br>RVPPGSRVRIRVNDDVKVNWHER |
| BH_2<br>SEQ ID NO: 2 | QHTRTYRLTPGEEQEFKYNTPMTMHVEVNTDVEIEYNGKEQRYPPGT<br>EVEIEVRPGTKVRIKVNTDVRVEIREN |
| BH_3<br>SEQ ID NO: 3 | PETRTYRFTPGEEREFEFDTNVEFRFDSDVEVTVNGQTTRVPPGSSV<br>EVPPGSRIRIRVNTDLQVEVRRR |
| BH_4<br>SEQ ID NO: 4 | PETKTYRFTPGEEREFEHDTNVKWKFNTDVEIERNGERTRFTPGEEV<br>EVPPGTRVRIRVNTDVQFTLERN |
| BH_5<br>SEQ ID NO: 5 | PERREIRLSPGERYTFTVDTDVQFRVEKPVRVRHDGTETEYKPGTHL<br>RLPPGTSVTFEVDTDVRFEIQRN |
| BH_6<br>SEQ ID NO: 6 | PERREIRLSPGERYTFTVDTPVQFRVEKPVRVRYDGTETELKPGSHL<br>RLPPGTSITFEVDTPVRFEIQRN |
| BH_7<br>SEQ ID NO: 7 | SRYEITGNPGTRVELRENPGSRVKSNAPGRSERNGEHRTWNPGESRT<br>SNRPSTMEVESDGPISIEIRE |
| BH_8<br>SEQ ID NO: 8 | ESKKITVNAGERMTLHLNAGTEVRSEGPGREHSNGQTQQWPPGSTIR<br>SDQPTTTTFESDRPLTLEVRQ |
| BH_9<br>SEQ ID NO: 9 | KTKTYTVNPGEKVTITMNPGDEMTAEGPVTSRARGQEQTVNPGETVR<br>VNEPGTFTLESDRPVTVKIQH |
| BH_10<br>SEQ ID NO: 10 | TRETKVTVNPGEEYEVKVNPGTRVEIQAKGPAEFEGGGTRTRLNPGE<br>SYKFENLTSQPLRIRLRNLSDTPIEFRIREE |
| BH_11<br>SEQ ID NO: 11 | SERREYEVNPGERMEFTINKGERFEEKTNRPMTVRVELDGREERYTA<br>TPGESISVQNNSDNPARVEIQNDSDEPVRVEVRRH |
| BH_12<br>SEQ ID NO: 12 | PIDVRIRMPPGSTFRVTIKTDVEVQVNKPVRVEHDGTRTEYKPGTHL<br>RIPPGSEVRFEVDTDVEFRFKVTDPETVKEMEEHAREHGLEYETRSD |
| BH_6_ss1<br>SEQ ID NO: 13 | PERRCIRLSPGERYTFTVDTPVCFRVEKPVRVRYDGTETELKPGSHL<br>CLPPGTSITFEVDTPVRFCIQRN |
| BH_6_ss2<br>SEQ ID NO: 14 | PERREICLSPGERYTFTVDTPVQFRVEKPVRVRYDGTETELKPGSHL<br>RLPPGTSITFEVDTPVCFEIQRN |
| BH_6_ss3<br>SEQ ID NO: 15 | PERREIRLSPGERYTFTVDTPVQFCVEKPVRVRYDGTETELKPGSCL<br>RLPPGTSITFEVDTPVRFEIQRN |
| BH_12_ss1<br>SEQ ID NO: 16 | PIDVRICMPPGSTFRVTIKTPVEVQVNKPVRVEYDGTRTELKPGSHL<br>RIPPGSEIRFEVDTPVCFREKVTDPETVKEMEEHAREHGLEYETRSD |
| BH_12_ss2<br>SEQ ID NO: 17 | PIDCRIRMPPGSTFRVTIKTPVEVQVNKPVRVEYDGTRTELKPGSHL<br>RIPPGSEIRFEVDTPVEFREKVTDPETVKEMEEHAREHGLEYECRSD |
| BH_12_ss3<br>SEQ ID NO: 18 | PIDCRIRMPPGSTFRVTIKTPVEVQVNKPVRVEYDGTRTELKPGSHL<br>RIPPGSEIRFEVDTPVEFRFKVTDPETVKECEEHAREHGLEYETRSD |
| BH_13<br>SEQ ID NO: 19 | NCDVRVRVPPGSEVRLTFKTDVRIEVKNPMEVRHDGTETRYTPGTHL<br>RIPPGSQVDERVNTDVEFHLEMDNPETAKEVEEQARRQGVEVEVRCQ |
| BH_10_K61V65<br>SEQ ID NO: 20 | TRETKVTVNPGEEYEVKVNPGTRVEIQAKGPAEFEGGGTRTRLNPGE<br>SYKFENLTSQPLRKRLRVLSDTPIEFRIREE |
| BH_10_K63V65<br>SEQ ID NO: 21 | TRETKVTVNPGEEYEVKVNPGTRVEIQAKGPAEFEGGGTRTRLNPGE<br>SYKFENLTSQPLRIRKRVLSDTPIEFRIREE |
| BH_10_K63<br>SEQ ID NO: 22 | TRETKVTVNPGEEYEVKVNPGTRVEIQAKGPAEFEGGGTRTRLNPGE<br>SYKFENLTSQPLRIRKRNLSDTPIEFRIREE |

TABLE 1-continued

| Design name | Amino acid sequence |
|---|---|
| BH_10_C6<br>SEQ ID NO: 23 | TRETKCTVNPGEEYEVKVNPGTRVEIQAKGPAEFEGGGTRTRLNPGE<br>SYKFENLTSQPLRIRLRNLSDTPIEFRIREE |
| BH_10_C39<br>SEQ ID NO: 24 | TRETKVTVNPGEEYEVKVNPGTRVEIQAKGPAEFEGGGCRTRLNPGE<br>SYKFENLTSQPLRIRLRNLSDTPIEFRIREE |

In one embodiment, the polypeptide comprises two beta-sheets packing against each other forming a double-stranded beta-helix formed by 8 antiparallel beta-strands, also known as the jelly roll structure, as described in detail in the examples that follow.

In one specific embodiment, the polypeptide comprise an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence selected from the group consisting of SEQ ID NOS: 10, 11, and 20-24.

In another embodiment, amino acid changes from the reference polypeptide do not include changes in proline residues present in the loop connections between beta strands. Loop proline residues help to maintain β-arch structures, as described in the examples that follow.

In a further embodiment, amino acid changes from the reference polypeptide do not include changes in polar amino acid residues present in the loop connections between beta strands capable of forming hydrogen bonds to the loop backbone. As shown in the examples that follow, β-arch loops that are structurally pre-organized with the polar groups making internal hydrogen bonding likely favor folding to the correct topology and contribute to stability by compensating for the loss of interactions with water of polar groups in the sidechains and backbone.

In a still further embodiment, amino acid changes from the reference polypeptide do not include changes in hydrophobic amino acid residues present in the loop connections and adjacent to the polar amino acid residues between beta strands capable of forming hydrogen bonds to the loop backbone. Such hydrophobic residues help stabilize the desired beta sheet structures.

In another embodiment, amino acid changes from the reference polypeptide do not include changes in hydrophobic amino acid residues stabilizing the polypeptide core. Any position with a hydrophobic amino acid corresponds to the polypeptide core.

In another embodiment, amino acid changes from the reference polypeptide are conservative amino acid substitutions.

As used here, "conservative amino acid substitution" means that:
  hydrophobic amino acids (Ala, Cys, Gly, Pro, Met, Sce, Sme, Val, Ile, Leu) can only be substituted with other hydrophobic amino acids;
  hydrophobic amino acids with bulky side chains (Phe, Tyr, Trp) can only be substituted with other hydrophobic amino acids with bulky side chains;
  amino acids with positively charged side chains (Arg, His, Lys) can only be substituted with other amino acids with positively charged side chains;
  amino acids with negatively charged side chains (Asp, Glu) can only be substituted with other amino acids with negatively charged side chains; and
  amino acids with polar uncharged side chains (Ser, Thr, Asn, Gln) can only be substituted with other amino acids with polar uncharged side chains.

In all of the above embodiments, the polypeptide may be linked with a detectable label. Any suitable detectable label can be used, including but not limited to fluorescent or bioluminescent proteins, radioactive moieties, etc. In another embodiment, the polypeptide may be immobilized on a surface, including but not limited to a bead, a nanoparticle, a microarray, glass slide, membrane, microplate, etc.

In another aspect the disclosure provides nucleic acids encoding the polypeptide of any embodiment or combination of embodiments of the disclosure. The nucleic acid may comprise single stranded or double stranded RNA or DNA in genomic or cDNA form, or DNA-RNA hybrids, each of which may include chemically or biochemically modified, non-natural, or derivatized nucleotide bases. Such nucleic acid sequences may comprise additional sequences useful for promoting expression and/or purification of the encoded polypeptide, including but not limited to polyA sequences, modified Kozak sequences, and sequences encoding epitope tags, export signals, and secretory signals, nuclear localization signals, and plasma membrane localization signals. It will be apparent to those of skill in the art, based on the teachings herein, what nucleic acid sequences will encode the polypeptides of the disclosure.

In a further aspect, the disclosure provides expression vectors comprising the nucleic acid of any aspect of the disclosure operatively linked to a suitable control sequence. "Expression vector" includes vectors that operatively link a nucleic acid coding region or gene to any control sequences capable of effecting expression of the gene product. "Control sequences" operably linked to the nucleic acid sequences of the disclosure are nucleic acid sequences capable of effecting the expression of the nucleic acid molecules. The control sequences need not be contiguous with the nucleic acid sequences, so long as they function to direct the expression thereof. Thus, for example, intervening untranslated yet transcribed sequences can be present between a promoter sequence and the nucleic acid sequences and the promoter sequence can still be considered "operably linked" to the coding sequence. Other such control sequences include, but are not limited to, polyadenylation signals, termination signals, and ribosome binding sites. Such expression vectors can be of any type, including but not limited plasmid and viral-based expression vectors. The control sequence used to drive expression of the disclosed nucleic acid sequences in a mammalian system may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). The expression vector must be replicable in the host organisms either as an episome or by integration into host chromosomal DNA. In various embodiments, the expression vector may comprise a plasmid, viral-based vector, or any other suitable expression vector.

In another aspect, the disclosure provides host cells that comprise the nucleic acids or expression vectors (i.e., episomal or chromosomally integrated) disclosed herein, and/or a cell expressing the polypeptide of any embodiment or combination of embodiments herein, wherein the host cells can be either prokaryotic or eukaryotic. The cells can be transiently or stably engineered to incorporate the expression vector of the disclosure, using techniques including but not limited to bacterial transformations, calcium phosphate co-precipitation, electroporation, or liposome mediated-, DEAE dextran mediated-, polycationic mediated-, or viral mediated transfection.

In another embodiment, the disclosure provides pharmaceutical compositions comprising:

(a) the polypeptide, nucleic acid, expression vector, host cell, or cell of any embodiment or combination of embodiments herein; and (b) a pharmaceutically acceptable carrier.

The pharmaceutical compositions of the disclosure can be used, for example, in the methods of the disclosure described below. The pharmaceutical composition may comprise in addition to the polypeptide or other active agent of the disclosure (a) a lyoprotectant; (b) a surfactant; (c) a bulking agent; (d) a tonicity adjusting agent; (e) a stabilizer; (f) a preservative and/or (g) a buffer.

In some embodiments, the buffer in the pharmaceutical composition is a Tris buffer, a histidine buffer, a phosphate buffer, a citrate buffer or an acetate buffer. The pharmaceutical composition may also include a lyoprotectant, e.g. sucrose, sorbitol or trehalose. In certain embodiments, the pharmaceutical composition includes a preservative e.g. benzalkonium chloride, benzethonium, chlorohexidine, phenol, m-cresol, benzyl alcohol, methylparaben, propylparaben, chlorobutanol, o-cresol, p-cresol, chlorocresol, phenylmercuric nitrate, thimerosal, benzoic acid, and various mixtures thereof. In other embodiments, the pharmaceutical composition includes a bulking agent, like glycine. In yet other embodiments, the pharmaceutical composition includes a surfactant e.g., polysorbate-20, polysorbate-40, polysorbate-60, polysorbate-65, polysorbate-80 polysorbate-85, poloxamer-188, sorbitan monolaurate, sorbitan monopalmitate, sorbitan monostearate, sorbitan monooleate, sorbitan trilaurate, sorbitan tristearate, sorbitan trioleaste, or a combination thereof. The pharmaceutical composition may also include a tonicity adjusting agent, e.g., a compound that renders the formulation substantially isotonic or isoosmotic with human blood. Exemplary tonicity adjusting agents include sucrose, sorbitol, glycine, methionine, mannitol, dextrose, inositol, sodium chloride, arginine and arginine hydrochloride. In other embodiments, the pharmaceutical composition additionally includes a stabilizer, e.g., a molecule which, when combined with a protein of interest substantially prevents or reduces chemical and/or physical instability of the protein of interest in lyophilized or liquid form. Exemplary stabilizers include sucrose, sorbitol, glycine, inositol, sodium chloride, methionine, arginine, and arginine hydrochloride.

The polypeptides, nucleic acids, expression vectors, host cells, and/or cells may be the sole active agent in the pharmaceutical composition, or the composition may further comprise one or more other active agents suitable for an intended use.

The polypeptides, nucleic acids, expression vectors, host cells, cells, and/or pharmaceutical compositions of the disclosure may be used for any suitable purpose, including but not limited to as scaffolds for virus capsids and antibodies; to transport hydrophobic molecules; for use in recognition and enzymatic processing of carbohydrates; or for incorporating metal, ligand-binding and active sites. Details are provided in the examples that follow.

In another aspect, the disclosure provides methods for designing polypeptides that form a double-stranded β-helix formed by 8 antiparallel β-strands, comprising the steps of any embodiment or combinations of embodiments disclosed herein. Details of exemplary design methods are provided in the examples that follow.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

EXAMPLES

Summary

β-sheet proteins carry out critical functions in biology, and hence are attractive scaffolds for computational protein design. Despite this potential, de novo design of all β-sheet proteins from first principles lags far behind the design of all-α or mixed αβ domains due to their non-local nature and tendency of exposed β-strand edges to aggregate. Through study of loops connecting unpaired β-strands (β-arches), we have identified a series of structural relationships between loop geometry, sidechain directionality and β-strand length that arise from hydrogen bonding and packing constraints on regular β-sheet structures. We use these rules to de novo design jelly-roll structures with double-stranded β-helices formed by 8 antiparallel β-strands. The structure of a hyperthermostable design closely matched the computational model, demonstrating accurate control over the β-sheet structure and loop geometry. Our results open the door to the design of a broad range of non-local β-sheet protein structures.

Results

Constraints on β-Arch Geometry

Figure 4:
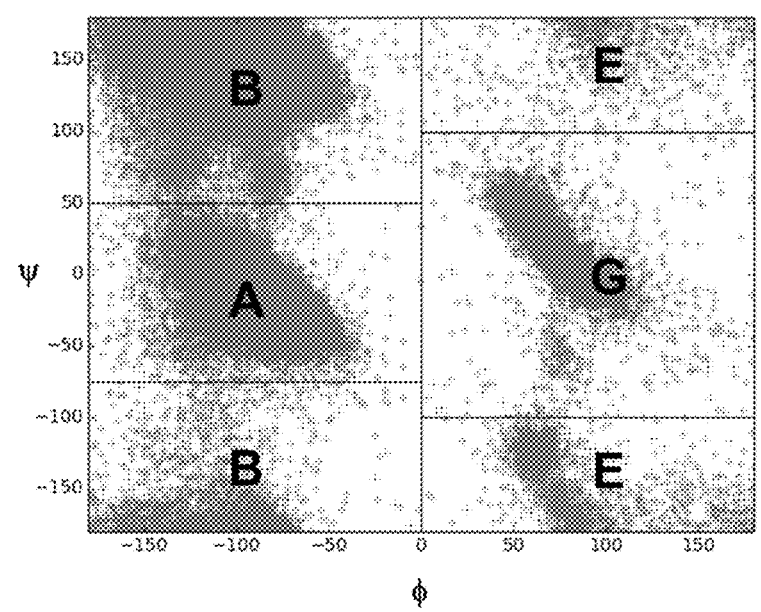
FIG. 4. Coarse-grained representation of the Ramachandran plot based on ABEGO torsion bins. ABEGO torsion bins provide a convenient way to classify the backbone geometry of protein residues based on the Ramachandran plot region of their φ/ψ dihedrals. "A" corresponds to the right-handed α-helix, "B" to the extended region typical of β-strands, "E" to the extended region with a positive φ dihedral, "G" to a left-handed α-helix (mostly accessible by L-glycine). The "O" bin is assigned for the cis peptide conformation (torsion around the peptide bond with the preceding residue, Cα(i)-N(i)-C(i−1)-Cα(i−1), below 90 degrees). Plotted data was collected from the residue torsional values of all β-arch loops from a non-redundant set of naturally occurring protein structures. Analysis of these loops revealed the sidechain pattern preferences of different loop ABEGO types, a critical feature for design.

We undertook the investigation of the constraints on the backbone geometry of β-strands and connecting loops that arise from hydrogen bonding and the requirement for a compact hydrophobic core. We studied sidechain directionality patterns of the two β-strand residues adjacent to β-arch loops (FIG. 1A, left) in naturally occurring protein structures, defining the sidechain orientation of the β-strand residue preceding the loop as concave (represented by "↓") if its CαCβ vector is parallel to the vector d from the first to the second β-strand, and convex (represented by "↑") if the CαCβ vector is antiparallel to d. For the residue following the loop the sidechain pattern is described in the same way, but instead using the vector from the second to the first β-strand (−d) as a reference (FIG. 1A). This results in four possible β-arch loop sidechain orientation patterns: "↑↑", "↑↓", "↓↑" and "↓↓". We analyzed the sidechain patterns and the local backbone geometry—as described with ABEGO torsion bins[16]—of 5,061 β-arch loops from a non-redundant database of natural protein structures (torsion bins "A" and "B" are the α-helix and extended regions, "G" and "E" regions are the positive φ angle equivalents of "A" and "B"; and "O" is the cis peptide bond conformation; FIG. 4). We found that all four sidechain orientation patterns frequently occur, and, in contrast to other types of loop connections (i.e. αβ, βα and β-hairpins)[5], there was not a correlation between β-arch loop length and sidechain pattern. Instead, each loop ABEGO type, because of the way in which it twists and bends the polypeptide chain[16], is associated with a specific flanking residue sidechain pattern (FIG. 1C). The most frequently observed turn types (between 1 and 5 amino acids) for each sidechain pattern are listed in FIG. 1D-E; for example ABB, BBGB, BABB and BGB are the most frequent loop types for the patterns "↓↓", "↓↑", "↑↓" and "↑↑", respectively.

The next level of non-local interaction complexity in all-β folds involves strand pairing (parallel or antiparallel) between two β-arches forming a β-arcade (FIG. 1F). Since the β-arch loops are stacked in-register, the sidechains adjacent to one β-arch loop are likely to have the same orientation as the sidechains adjacent to the second β-arch loop; analysis of naturally occurring β-arcades confirms that the sidechain patterns of the two β-arch loops indeed are correlated (FIG. 1G).

Jelly-Roll Design Principles

Figure 2:
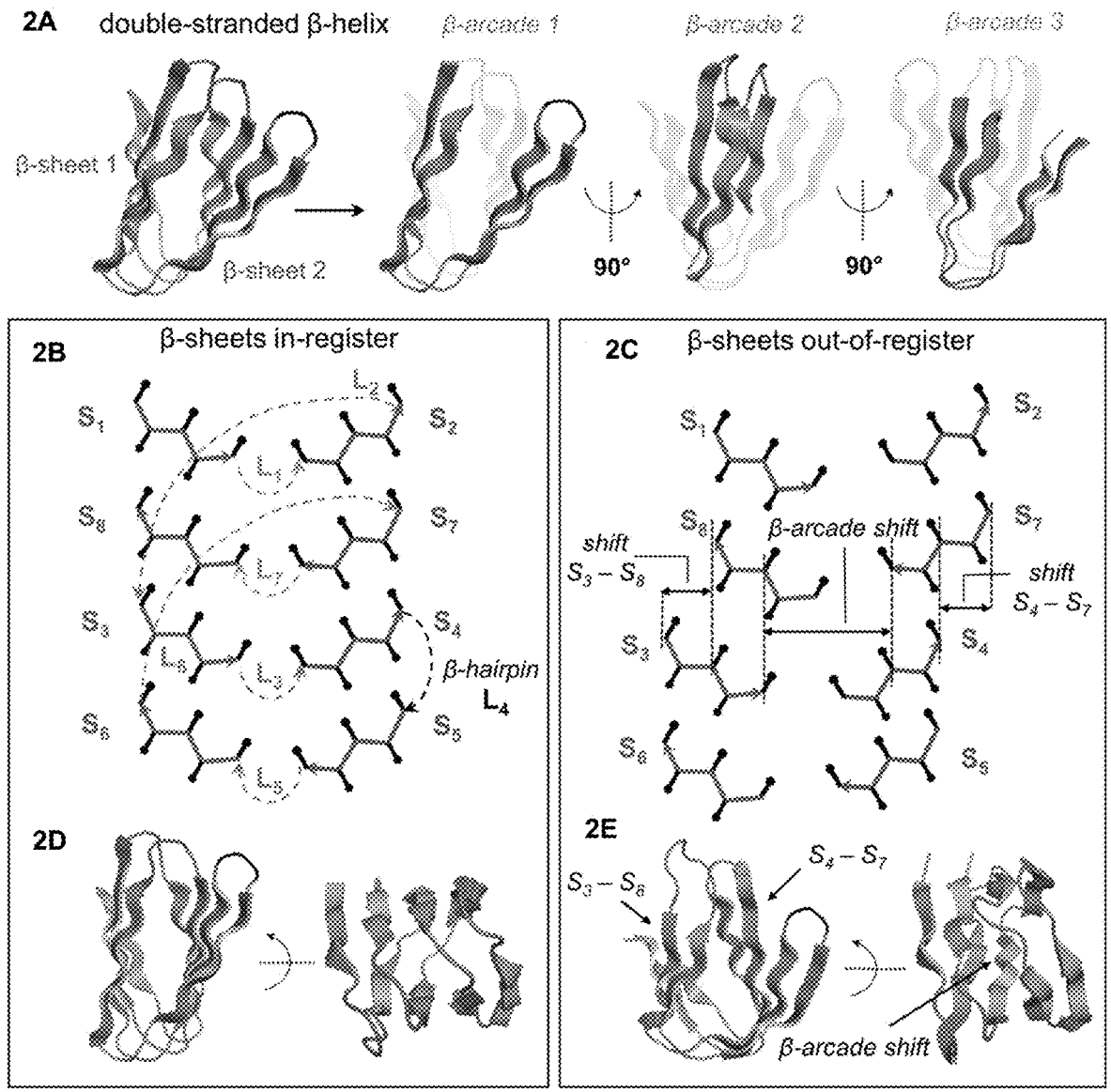
FIG. 2A-2E. Double-stranded β-helix topology specification. (A) The double-stranded β-helix fold consists of two 4-stranded antiparallel β-sheets with 6 β-arch and 1β-hairpin connections. Pairs of β-arches forming the three β-arcades are highlighted on the right. (B) Topology diagram of a designed double-stranded 3-helix with all β-strand pairs in register. Sidechain Cβ positions oriented toward the inner and outer faces of the β-helix are represented with up and down black arrows with rounded tips, respectively. (C) Definition of β-arcade register shift varied during conformational sampling. The β-arcade register shift (between β-arcades 1 and 3) is determined by the register of β-strand pairs $S_3/S_8$ and $S_4/S_7$, and the lengths of β-strands $S_3$, $S_4$, $S_8$ and $S_7$ (Methods). In this example β-strand pairs $S_3/S_8$ and $S_4/S_7$ each have a two residue register shift, resulting in an overall β-arcade register shift of 4 residues. Loops are omitted to facilitate visualization. (D) Example of a design model with all β-strand pairs in register forming a sandwich-like structure. (E) Example of a design model with register shifts between β-arcades 1 and 3 forming a barrel-like structure.

The double-stranded β-helix can be regarded as a long β-hairpin wrapped around an axis perpendicular to the direction of β-strands, with β-helical turns formed by the pairing between β-arcades (FIG. 2A). In the compact folded structure, two antiparallel β-sheets pack against each other in a sandwich-like arrangement, with the first strand paired to the last, and all β-strands are connected through β-arch loops except for the central β-hairpin. We aimed at designing β-helices with 3 β-arcades forming two antiparallel 4-stranded β-sheets, with the 8 β-strands connected through 6 β-arches and 1 β-hairpin. The non-local character of the structure grows from the first β-arcade, which starts from the central β-hairpin, to the last one, where the N- and C-termini are paired.

The analysis from FIG. 1 leads to strong constraints on the construction of β-sheet backbone structures, as the sidechain directionality patterns of the β-strands and loops are coupled in several ways. First, the directionality patterns of the loops preceding and following each β-strand are coupled to the length of the strand (FIG. 2B): for example, a β-strand with an even number of residues that is preceded by a "↑↑" loop must be followed by a "↓↑" or a "↓↓" loop, but not a "↑↑" or "↑↓" loop, due to the alternating pleating of β-strands. Second, since the β-arcades of the β-helix have paired β-strands and β-arch loops, the sidechains adjacent to one β-arch loop must have the same orientation as the paired sidechains adjacent to the second β-arch loop (FIG. 1F). Due to the antiparallel orientation of the β-arcades, "↓↓" and "↑↑" loops are compatible with loops of the same type, but "↑↓" loops are only compatible with" ↓↑" (FIG. 1F). Third, the twist and curvature of the two β-sheets of the β-helix is constrained by the hydrogen bonding register between β-arcades 1 and 3 (herein called β-arcade register), and within β-strand pairs $S_3/S_8$ and $S_4/S_7$, as shown in FIG. 2C.

De Novo Design of Protein Structures

We constructed double-stranded β-helix protein backbones by Monte Carlo fragment assembly using blueprints—representations of the target protein topologies specifying the ordering, lengths and backbone torsion bins of secondary structure elements and loop connections[5]—in conjunction with backbone hydrogen-bonding constraints specifying all pairings between β-strands. We explored strand lengths between 5 and 7 residues and the most commonly observed β-arch loops between 3 and 5 residues (FIG. 1D). The central β-hairpin was designed with two-residue loops following the ββ-rule[5]. The register shifts between pairs of β-strands from different β-arcades (1 and 3) were allowed to range from 0 to 2 and the β-arcade register shifts between 0 and 4; strand pairs within the same β-arcade were kept in-register. A total of 3,673 combinations were enumerated, of which 1,853 had mutually compatible strand lengths and loop types consistent with the constraints summarized in the previous paragraph. For each of these internally consistent blueprints, we used Rosetta™ to build thousands of protein backbones. The resulting ensemble of backbone structures has considerable structural diversity; those with all strands in-register had narrow sandwich-like structures (FIG. 2D), while those with large register shifts had wider barrel-like structures (FIG. 2E).

For each generated backbone, we carried out flexible-sequence design calculations to identify low-energy amino acid identities and sidechain conformations providing close complementary packing, sidechain-backbone hydrogen bonding in β-arch loops—to pre-organize their conformation and facilitate folding—and high sequence-structure compatibility. We favored inward-pointing charged or polar amino acids at the four edge strands to minimize aggregation propensity. Loop sequences were designed with consensus profiles obtained from fragments with the same backbone ABEGO torsion bins[21]. Because the very large size of the space sampled by our design procedure limits convergence on optimal sequence-structure pairs, we carried out a second round of calculations starting from the blueprints yielding the lowest energy designs, intensifying sampling at both the backbone and sequence level. For a subset of designs, we introduced disulfide bonds between paired β-strand positions with high sequence separation (e.g. between the first and last β-strands) and optimal orientation (see Methods)—disulfide bonds distant in primary sequence decrease the entropy of the unfolded state and therefore enhance the thermodynamic stability of the native state. To assess compatibility of the top ranked designed sequences with their structures we characterized their folding energy landscape with biased forward folding simulations, and those with substantial near-native sampling were subsequently assessed by Rosetta™ ab initio structure prediction calculations. Designs with funnel-shaped energy landscapes—where the designed structure is at the global energy minima and has a substantial energy gap with respect to alternative conformations—were selected for experimental characterization. Ab initio structure prediction of natural β-sheet proteins tends to oversample local contacts (i.e. favoring β-hairpins over β-arches), but we succeeded in designing sequences with the β-arches sufficiently strongly encoded that they folded in silico to near the designed target structure.

Experimental Characterization

Figure 3:
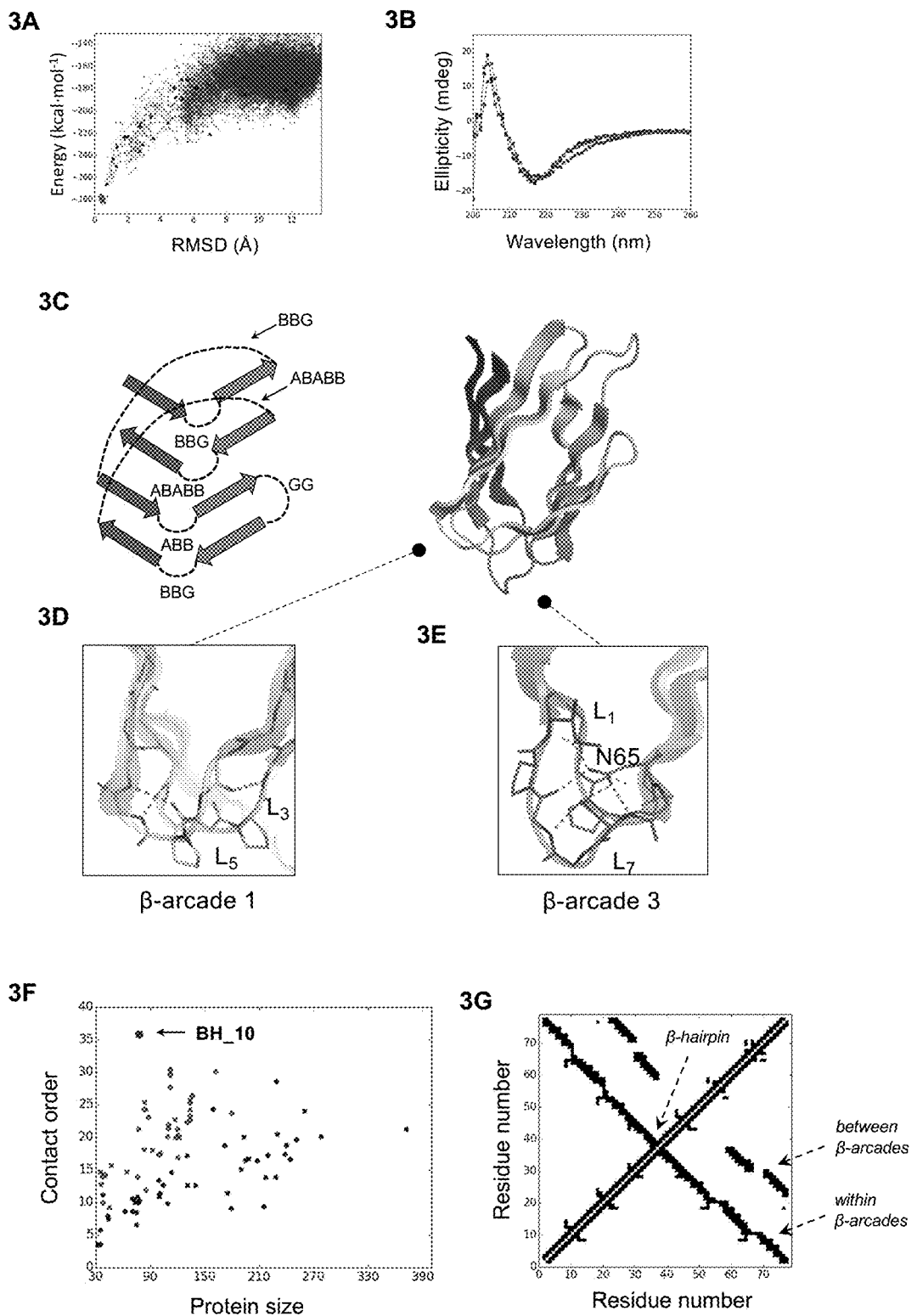
FIG. 3A-3G. Computational design and characterization of BH_10. (A) Calculated BH_10 folding energy landscape. Each dot represents the lowest energy structure obtained from ab initio folding trajectories starting from an extended chain, biased forward folding trajectories or local relaxation of the designed structure; x-axis is the Cα-root mean squared deviation (RMSD) from the designed model; the y-axis, the Rosetta™ all-atom energy. (B) Far-ultraviolet circular dichroism spectra. (C) Design model. The topology scheme of the design model is shown on the left, describing ABEGO torsion bins of all loop connections. (D) Backbone hydrogen bonding of β-arcade 1. (E) Sidechain interactions of N65 with backbone and sidechains form a hydrogen-bonded network in β-arcade 3. (F) Contact order of de novo protein domains computationally designed to date confirmed by high resolution structure determination; all-α, αβ and all-β. BH_10 stands out with a contact order of 35.8 for a chain length of 78 residues. (G) Contact map illustrating the large sequence separation of the contacts present in the BH_10 topology.
Figure 5:
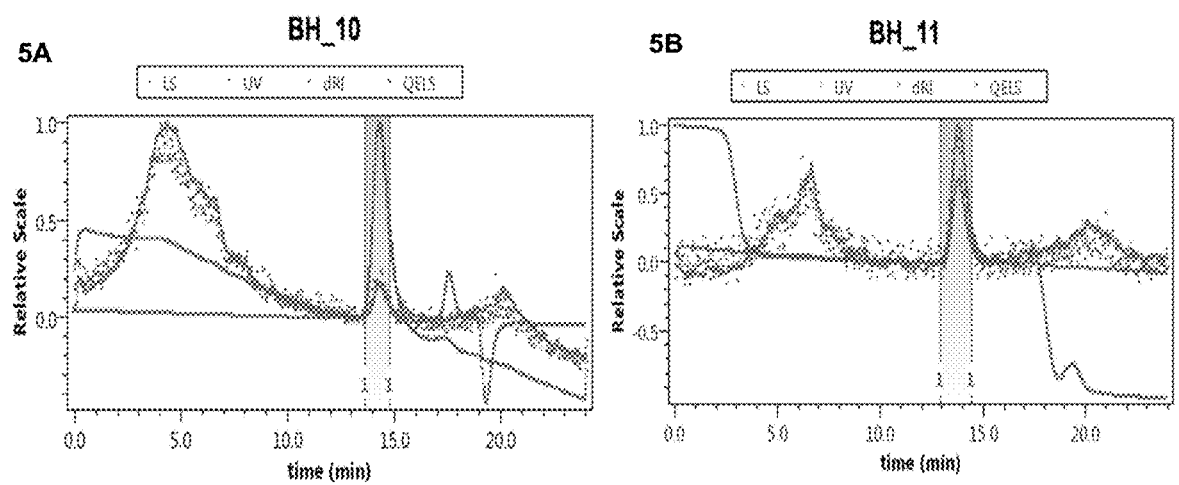
FIG. 5A-5B. SEC-MALS analysis of (A) BH_10 and (B) BH_11 designs. Both proteins are monodisperse and have estimated molecular weights in good agreement with the theoretical value of the monomers.
Figure 6:
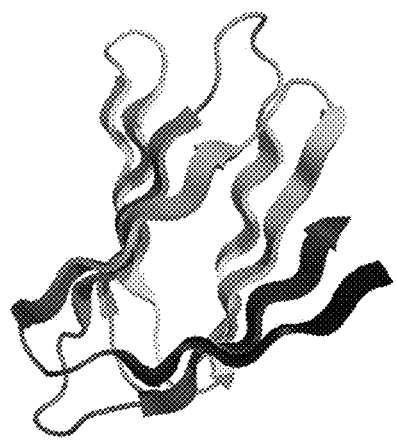
FIG. 6A-6C. Experimental characterization of the designed protein BH_11. (A) Cartoon representation of the design model. (B) Calculated folding energy landscape. Each dot represents the lowest energy structure obtained from ab initio folding trajectories starting from an extended chain, biased forward folding trajectories or local relaxation of the designed structure; x-axis shows the Cα-root mean squared deviation (RMSD) from the designed model; the y-axis shows the Rosetta™ all-atom energy. (C) Far-ultraviolet circular dichroism spectra.
Figure 6:
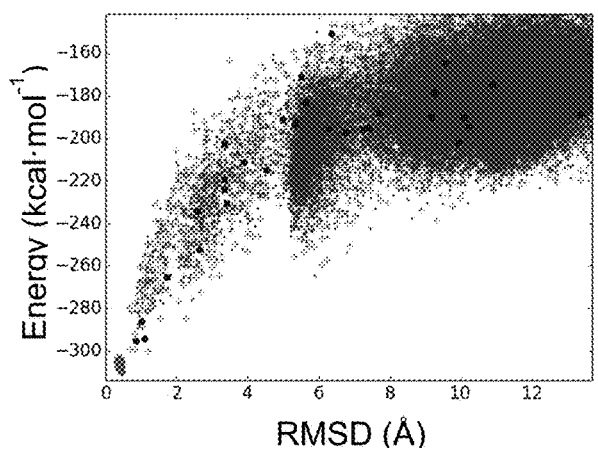
Figure 6:
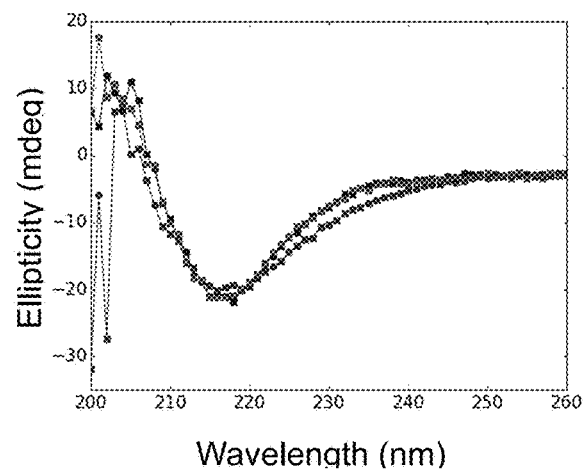

We chose for experimental characterization 19 designs with funnel-shaped energy landscapes ranging between 70 and 94 amino acids (Table 2). BLAST searches[26,27] indicated that the designed sequences had little or no similarity with native proteins (lowest E-values ranging from 0.003 to >10; Table 3). Synthetic genes encoding the designs (design names are BH_n; where "BH" stands for β-helix and "n" the design number; and a "_ss" suffix if disulfide bonds are present) were obtained, the proteins were expressed in *Escherichia coli*, and purified by affinity chromatography. 16 of the designs expressed well and were soluble, and two (BH_10 and BH_11) were monomeric (FIG. 5) by size-exclusion chromatography coupled with multi-angle light scattering (SEC-MALS) (most of the non-monomeric designs were either dimers or soluble aggregates). Both monomeric designs had far-ultraviolet circular dichroism spectrum (CD) at 25° C. characteristic of β proteins and a melting temperature ($T_m$) above 95° C. (FIG. 3A-B and FIG. 6).

TABLE 2

Designed protein sequences. The lowest E-value obtained from BLAST searches (against the NCBI nr database of non-redundant protein sequences) is shown.

| Design name | Amino acid sequence | E-value |
|---|---|---|
| BH_1<br>SEQ ID NO: 1 | PETKTYRFTPGEEREYEENTDVEVEVNHDMEITVNGQTQRYTPGTSV<br>RVPPGSRVRIRVNDDVKVNWHER | 3.2 |
| BH_2<br>SEQ ID NO: 2 | QHTRTYRLTPGEEQEFKYNTPMTMHVEVNTDVEIEYNGKEQRYPPGT<br>EVEIEVRPGTKVRIKVNTDVRVEIRE**N | 2.8 |
| BH_3<br>SEQ ID NO: 3 | PETRTYRFTPGEEREFEFDTNVEFRFDSDVEVTVNGQTTRVPPGSSV<br>EVPPGSRIRIRVNTDLQVEVRRR | 1.1 |
| BH_4<br>SEQ ID NO: 4 | PETRTYRFTPGEEREFEHDTNVKWKFNTDVEIERNGERTRFTPGEEV<br>EVPPGTRVRIRVNTDVQFTLERN | 3.6 |
| BH_5<br>SEQ ID NO: 5 | PERREIRLSPGERYTFTVDTDVQFRVEKPVRVRHDGTETEYKPGTHL<br>RLPPGTSVTFEVDTDVRFEIQRN | 0.016 |
| BH_6<br>SEQ ID NO: 6 | PERREIRLSPGERYTFTVDTPVQFRVEKPVRVRYDGTETELKPGSHL<br>RLPPGTSITFEVDTPVRFEIQRN | 0.011 |
| BH_7<br>SEQ ID NO: 7 | SRYEITGNPGTRVELRENPGSRVKSNAPGRSERNGEHRTWNPGESRT<br>SNRPSTMEVESDGPISIEIRE** | 0.8 |
| BH_8<br>SEQ ID NO: 8 | ESKKITVNAGERMTLHLNAGTEVRSEGPGREHSNGQTQQWPPGSTIR<br>SDQPTTTTFESDRPLTLEVR**Q | 3.5 |
| BH_9<br>SEQ ID NO: 9 | KTKTYTVNPGEKVTITMNPGDEMTAEGPVTSRARGQEQTVNPGETVR<br>VNEPGTFTLESDRPVTVKIQ**H | >10 |
| BH_10<br>SEQ ID NO: 10 | TRETKVTVNPGEEYEVKVNPGTRVEIQAKGPAEFEGGGTRTRLNPGE<br>SYKFENLTSQPLRIRLRNLSDTPIEFRIREE | 6.3 |
| BH_11<br>SEQ ID NO: 11 | SERREYEVNPGERMEFTINKGERFEEKTNRPMTVRVELDGREERYTA<br>TPGESISVQNNSDNPARVEIQNDSDEPVRVEVRRH | 4.5 |
| BH_12<br>SEQ ID NO: 12 | PIDVRIRMPPGSTFRVTIKTDVEVQVNKPVRVEHDGTRTEYKPGTHL<br>RIPPGSEVRFEVDTDVEFREKVTDPETVKEMEEHAREHGLEYETRSD | 1.0 |
| BH_6_ss1<br>SEQ ID NO: 13 | PERRCIRLSPGERYTFTVDTPVCFRVEKPVRVRYDGTETELKPGSHL<br>CLPPGTSITFEVDTPVRFCIQRN | 0.013 |
| BH_6_ss2<br>SEQ ID NO: 14 | PERREICLSPGERYTFTVDTPVQFRVEKPVRVRYDGTETELKPGSHL<br>RLPPGTSITFEVDTPVCFEIQRN | 0.003 |
| BH_6_ss3<br>SEQ ID NO: 15 | PERREIRLSPGERYTFTVDTPVQFCVEKPVRVRYDGTETELKPGSCL<br>RLPPGTSITFEVDTPVRFEIQRN | 0.012 |
| BH_12_ss1<br>SEQ ID NO: 16 | PIDVRICMPPGSTFRVTIKTPVEVQVNKPVRVEYDGTRTELKPGSHL<br>RIPPGSEIRFEVDTPVCFREKVTDPETVKEMEEHAREHGLEYETRSD | 0.98 |
| BH_12_ss2<br>SEQ ID NO: 17 | PIDCRIRMPPGSTFRVTIKTPVEVQVNKPVRVEYDGTRTELKPGSHL<br>RIPPGSEIRFEVDTPVEFREKVTDPETVKEMEEHAREHGLEYECRSD | 6.8 |
| BH_12_ss3<br>SEQ ID NO: 18 | PIDCRIRMPPGSTFRVTIKTPVEVQVNKPVRVEYDGTRTELKPGSHL<br>RIPPGSEIRFEVDTPVEFRFKVTDPETVKECEEHAREHGLEYETRSD | 7.7 |
| BH_13<br>SEQ ID NO: 19 | NCDVRVRVPPGSEVRLTFKTDVRIEVKNPMEVRHDGTETRYTPGTHL<br>RIPPGSQVDFRVNTDVEFHLEMDNPETAKEVEEQARRQGVEVEVRCQ | 1.9 |

The two monomeric designs with well-ordered structures were among those with better packed cores and a larger proportion of β-arch loops containing prolines and hydrogen bonding satisfying the backbone polar atoms (Table 3). β-arch loops that are structurally pre-organized with the polar groups making internal hydrogen bonding likely favor folding to the correct topology and contribute to stability by compensating for the loss of interactions with water of polar groups in the sidechains and backbone. These interactions could also disfavor the competing local strand pairing arrangement in which the two strands form a β-hairpin—this is a very common pathology in ab initio structure prediction[25]. For the most stable dimeric design (BH_6) we introduced disulfide bonds to stabilize protein regions having contacts with large sequence separation—e.g. between the N- and C-terminal strands—but this did not succeed in yielding stable monomers. Addition of an α-helix to the C-termini (one of the two extremes of the β-helix) as a capping domain protecting the strand edges from intermolecular pairing also failed to yield stable monomers, even in combination with disulfide bonds. This suggests that the sequence of the core β-sheet must strongly encode its structure independent of disulfide bonds or protecting domains aimed at increasing stability.

TABLE 3

Computed scores for experimentally characterized designs. Hydrogen bonding (hbond_bb_sc, hbond_lr_bb and hbond_sr_bb) and backbone torsional (rama) energy scores were averaged over all loop residue positions, and the fa_atr score term accounting for attractive Van der Waals interactions was averaged over all residues. Designs in the table were ranked based on "hbond_sum" (sum of the three hydrogen bonding average scores), rama (sum of the rama scores average over loop residue positions) and "loops w/Pro" (number of loops containing at least one proline). Designs with substantially higher fa_atr scores (indicative of underpacked hydrophobic cores) were placed at the end of the ranking (BH_7, BH_9 and BH_8). Only those designs without disulfide bonds or extra helical domains were considered in this analysis. The two monomeric designs with well-ordered structures (BH_10 and BH_11) are those with the best compromise of the three scores considered.

| Design name | hbond_sum | hbond_bb_sc | hbond_lr_bb | hbond_sr_bb | rama | loops w/Pro | fa_atr |
|---|---|---|---|---|---|---|---|
| BH_11 | −0.651 | −0.220 | −0.328 | −0.103 | −0.161 | 5 | −4.510 |
| BH_10 | −0.556 | −0.109 | −0.348 | −0.099 | −0.142 | 6 | −4.334 |
| BH_2 | −0.557 | −0.120 | −0.391 | −0.046 | −0.138 | 4 | −4.557 |
| BH_1 | −0.545 | −0.086 | −0.406 | −0.053 | −0.150 | 3 | −4.609 |
| BH_3 | −0.547 | −0.076 | −0.429 | −0.042 | −0.113 | 3 | −4.367 |
| BH_6 | −0.531 | −0.073 | −0.396 | −0.061 | −0.085 | 6 | −4.478 |
| BH_4 | −0.515 | −0.055 | −0.337 | −0.124 | −0.137 | 3 | −4.679 |
| BH_5 | −0.535 | −0.077 | −0.395 | −0.063 | −0.088 | 4 | −4.575 |
| BH_7 | −0.617 | −0.162 | −0.333 | −0.122 | −0.125 | 6 | −3.691 |
| BH_9 | −0.557 | −0.094 | −0.344 | −0.120 | −0.104 | 6 | −3.652 |
| BH_8 | −0.622 | −0.150 | −0.338 | −0.134 | −0.087 | 4 | −3.842 |

Structure of a De Novo Designed β-Helix

Figure 7:
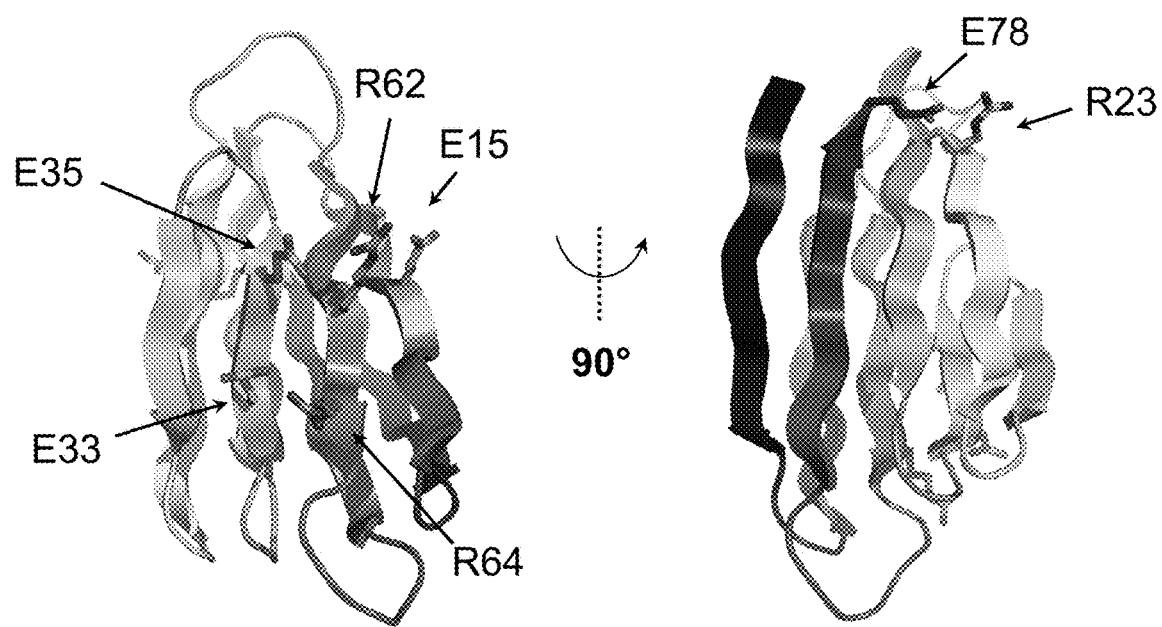
FIG. 7. Surface salt bridges of design BH_10. Salt bridges of the computational model. Most of these salt bridges correspond to residues involved in the pairing between β-arcades 1 and 3 (E33:R64, E35:R62 and E78:R23).
Figure 8:
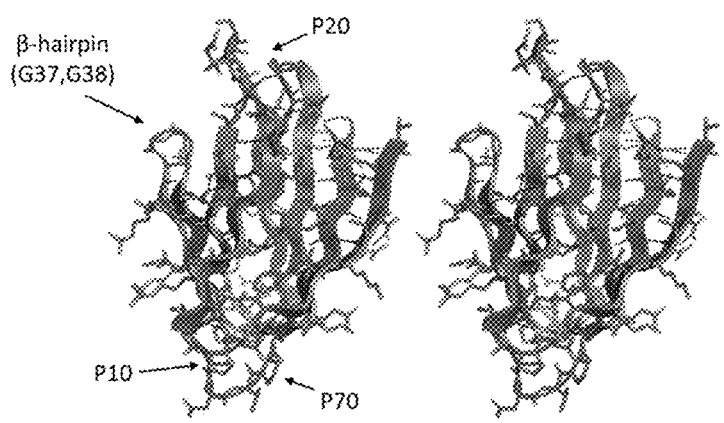
FIG. 8A-8B. Loop sequences and patterns of design BH_10. (A) designed protein sequence (SEQ ID NO:10) and ABEGO strings of loops (β-strands, β-arches and the β-hairpin). Critical residues determining the sidechain patterns of β-arches are highlighted. (B) All-atom stereo representation of the design with backbone hydrogen bonding and salt bridge interactions highlighted. Critical loop positions, such as prolines in β-arches or the central β-hairpin residues, are also indicated.

The structure of BH_10 was confirmed by NMR spectroscopy (data not shown) and found it to be in very close agreement with the computational model (Cα-RMSD 0.84 Å, data not shown). The overall topology is accurately recapitulated, including all strand pairings, register shifts and loop connections. The designed aliphatic and aromatic sidechain packing in the protein core as well as salt bridge interactions across the two β-sheet surfaces were also accurately reproduced—three salt bridges between the two paired β-arcades and one within the third β-arcade are well supported (FIG. 7). The agreement both in the backbone conformation and hydrogen-bonding interactions of the loops forming the three β-arcades is remarkable, given that these elements are the most flexible parts of the structure and therefore difficult to design due to sampling bottlenecks. The β-arcades were designed with pairs of β-arch loops that mutually interact via backbone-backbone hydrogen bonds—due to the complementarity between their backbone conformations—stabilizing loop pairing and avoiding burial of polar backbone atoms (see FIG. 8 for the BH_10 loop sequences and sidechain patterns). For example, β-arcade 1 is formed by 'BBG' and 'ABB' loops, and the buried backbone NH group of the 'G' position in the former makes a hydrogen bond with the buried backbone C=O of the neighboring loop (FIG. 3D). The other two β-arcades were designed with one β-arch loop containing buried and fully hydrogen-bonded asparagines (4 hydrogen bonds in total) that stabilize both loop pairing and the local β-arch conformation (of 'ABABB' loops) (FIG. 3E). By design, the asparagine sidechain geometry was further stabilized with hydrophobic stacking interactions from the two β-arch loops of the same arcade.

The amino acid sequence of BH_10 is unrelated to any sequence in the NCBI nr database. We searched the PDB for similarities in structure or sequence (with HHpred[30] for sensitive profile based sequence search), and identified matches similar in fold but containing additional and irregular secondary structures, and longer loops. These matches are all homodimers with sheet-to-sheet interface packing (FIG. 9) or domains integrated in larger structures, in sharp contrast to the BH_10 monomer.

Contact Order and Sequence Determinants of the BH_10 Fold

The non-local character of BH_10 is of particular note—a large fraction of the contacting residues are distant along the linear sequence, with extensive strand pairing between the N and C-terminal β-strands. The contact order of the structure—the average separation along the linear sequence of residues in contact in the three dimensional structure—is higher than any previous single-domain protein designed de novo (FIG. 3F-G). High contact order proteins fold more slowly than low contact order proteins as there is a greater loss in chain entropy for forming the first native interactions, and they tend to form long-lived non-native structures that can oligomerize or aggregate[31]. We have overcome the challenges in designing non-local structures by focusing on backbones lacking internal strain and having maximal internal coherence, and programming β-strand orientation with highly structured loops.

Figure 10:
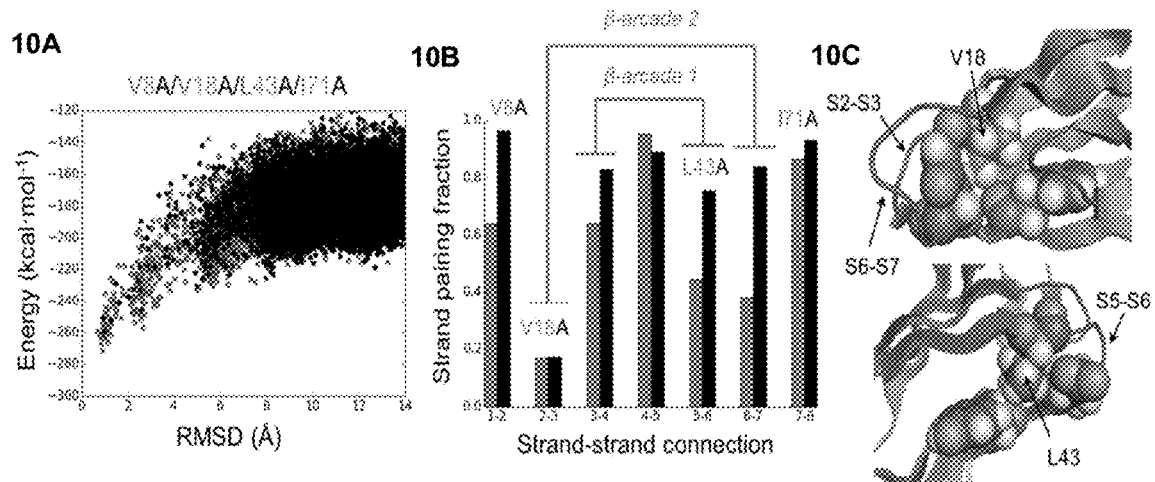
FIG. 10A-10I. Sequence determinants of β-arch formation. For the energy landscapes of different types of mutations we calculated the frequency of formation of β-hairpins between every two consecutive β-strands. Increases of β-hairpin formation were correlated with a decrease of near native sampling. (A, D, G, I) Calculated energy landscapes for mutants assessing different types of interactions are compared with the landscape of BH_10. (B, E, H) Effect of mutations on β-strand pairing. Mutated loop connections are labeled with the corresponding amino acid substitution. Most of the mutations increase sampling of more local β-hairpin connections. Connection S4-S5 corresponds to the central β-hairpin of the β-helix. (C) Sidechain packing interactions stabilizing β-arch loop connections that when mutated to alanine decrease β-arch stability and favor β-hairpin sampling. Mutant V18A favors hairpin sampling in the neighboring β-arch of the same β-arcade. (F) Sidechain-backbone hydrogen-bonding interactions stabilizing β-arch loop geometry; upon removal by alanine substitutions β-hairpin sampling increases. (E) Mutations in the S6-S7 and S7-S8 connections favors sampling of β-hairpins between S6 and S8.
Figure 10:
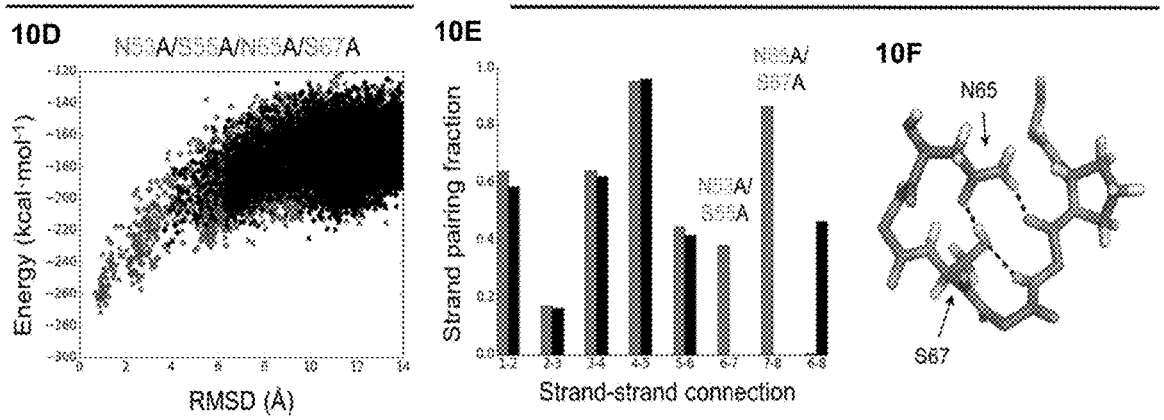
Figure 10:
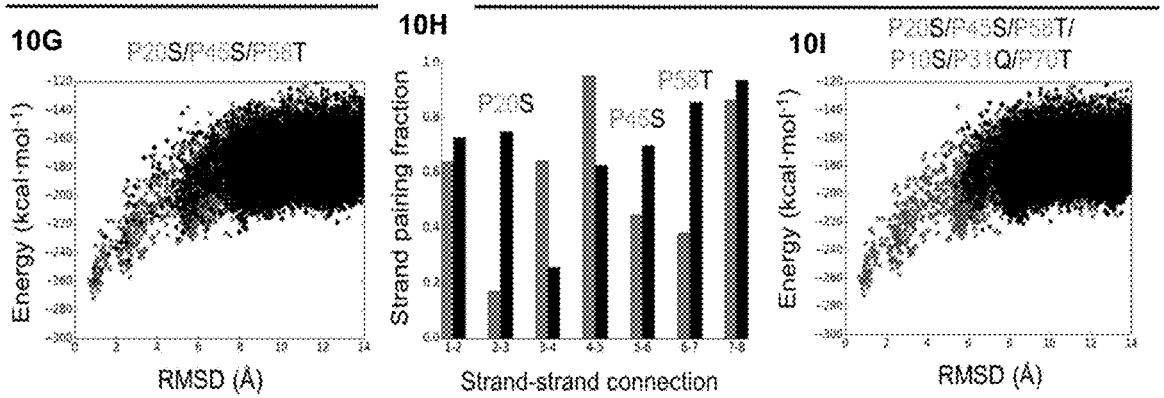

One of the challenges in achieving high contact order through β-arches is to disfavor competing more sequence-local β-hairpins. To evaluate in silico how each of our design features contribute to favoring β-arches over β-hairpins, we generated folding energy landscapes for a series of mutants of BH_10 that disrupt, one at a time, loop hydrogen bonding, sidechain packing of loop neighbors and loop local geometry. For all conformations generated, we classified all the β-strand connections as β-arch or β-hairpin depending on strand pairing formation, and calculated the overall frequency of β-hairpin formation for each pair of consecutive β-strands. As shown in FIG. 10, disruption of packing within or between β-arch loops, removal of sidechain-backbone hydrogen bonding interactions and reducing loop geometry encoding by eliminating prolines all increase sampling of competing β-hairpin conformations, and thus substantially decrease sampling of β-arches and the target designed structure.

Discussion

The design of all-β globular proteins from first principles has remained elusive for two decades of protein design research. We have successfully designed a double-stranded β-helix de novo, as confirmed by structure studies of the design BH_10, based on a series of rules describing the geometry of β-arch loops and their interactions in more complex β-arcades. Our work also achieves two related milestones: the first accurate design of an all-β globular protein with exposed β-sheet edges, and the most non-local structure yet designed from scratch. Comparison between successful and failed designs suggests folding and stabilization of the monomeric structure (and implicitly, disfavoring of competing topologies with more local strand pairings) is bolstered by loops containing sidechain-backbone and backbone-backbone hydrogen bonds together with well-packed mixed aliphatic/aromatic sidechains in the protein core, inward-pointing polar amino acids at strand edges and salt bridges between paired strands. The β-helix fold here designed is well suited for incorporating metal, ligand-binding and active sites. With the basic design principles now understood, our de novo design strategy should enable the construction of a wide range of β-helix structures tailored to a broad diversity of target ligands.

The design rules described here are a considerable advance as they provide control over β-arch connections between distinct β-sheets, and enable the design of a broad range of β-protein families beyond the β-barrel and β-helix with considerable medical and biotechnological potential; for example the immunoglobulin fold widely utilized for binding and loop scaffolding in nature is topologically very similar to the double-stranded β-helices designed here, with a larger proportion of β-hairpins over β-arches.

REFERENCES

1. Kortemme, T., Ramirez-Alvarado, M. & Serrano, L. Design of a 20-amino acid, three-stranded beta-sheet protein. *Science* 281, 253-256 (1998).
2. Searle, M. S. & Ciani, B. Design of beta-sheet systems for understanding the thermodynamics and kinetics of protein folding. *Curr. Opin. Struct. Biol.* 14, 458-464 (2004).
3. Hughes, R. M. & Waters, M. L. Model systems for beta-hairpins and beta-sheets. *Curr. Opin. Struct. Biol.* 16, 514-524 (2006).
4. Marcos, E. & Adriano-Silva, D. Essentials of de novo protein design: Methods and applications. *WIREs Comput Mol Sci* e1374 (2018).
5. Koga, N. et al. Principles for designing ideal protein structures. *Nature* 491, 222-227 (2012).
6. Hecht, M. H. De novo design of beta-sheet proteins. *Proceedings of the National Academy of Sciences* 91, 8729-8730 (1994).
7. Plaxco, K. W., Simons, K. T. & Baker, D. Contact order, transition state placement and the refolding rates of single domain proteins. *J. Mol. Biol.* 277, 985-994 (1998).
8. Quinn, T. P., Tweedy, N. B., Williams, R. W., Richardson, J. S. & Richardson, D. C. Betadoublet: de novo design, synthesis, and characterization of a beta-sandwich protein. *Proc. Nat. Acad. Sci. U.S.A.* 91, 8747-8751 (1994).
9. Nanda, V. et al. De novo design of a redox-active minimal rubredoxin mimic. *J. Am. Chem. Soc.* 127, 5804-5805 (2005).
10. Dou, J. et al. De novo design of a fluorescence-activating β-barrel. *Nature* (2018). doi:10.1038/s41586-018-0509-0
11. Voet, A. R. D. et al. Computational design of a self-assembling symmetrical β-propeller protein. *Proceedings of the National Academy of Sciences* 111, 15102-15107 (2014).
12. MacDonald, J. T. et al. Synthetic beta-solenoid proteins with the fragment-free computational design of a beta-hairpin extension. *Proceedings of the National Academy of Sciences* 113, 10346-10351 (2016).
13. Ottesen, J. J. & Imperiali, B. Design of a discretely folded mini-protein motif with predominantly beta-structure. *Nat. Struct. Biol.* 8, 535-539 (2001).
14. Hu, X., Wang, H., Ke, H. & Kuhlman, B. Computer-based redesign of a beta sandwich protein suggests that extensive negative design is not required for de novo beta sheet design. *Structure* 16, 1799-1805 (2008).
15. Hennetin, J., Jullian, B., Steven, A. C. & Kajava, A. V. Standard conformations of beta-arches in beta-solenoid proteins. *J. Mol. Biol.* 358, 1094-1105 (2006).
16. Lin, Y.-R. et al. Control over overall shape and size in de novo designed proteins. *Proc. Nat. Acad. Sci. U.S.A.* 112, E5478-85 (2015).
17. Kajava, A. V., Baxa, U. & Steven, A. C. β arcades: recurring motifs in naturally occurring and disease-related amyloid fibrils. *The FASEB Journal* 24, 1311-1319 (2010).
18. Kuhlman, B. & Baker, D. Native protein sequences are close to optimal for their structures. *Proc. Nat. Acad. Sci. U.S.A.* 97, 10383-10388 (2000).
19. Kuhlman, B. et al. Design of a novel globular protein fold with atomic-level accuracy. *Science* 302, 1364-1368 (2003).
20. Richardson, J. S. & Richardson, D. C. Natural-sheet proteins use negative design to avoid edge-to-edge aggregation. *Proceedings of the National Academy of Sciences* 99, 2754-2759 (2002).
21. Marcos, E. et al. Principles for designing proteins with cavities formed by curved β sheets. *Science* 355, 201-206 (2017).
22. Rohl, C. A., Strauss, C. E. M., Misura, K. M. S. & Baker, D. Protein structure prediction using Rosetta. *Methods Enzymol.* 383, 66-93 (2004).
23. Bradley, P. Toward High-Resolution de Novo Structure Prediction for Small Proteins. *Science* 309, 1868-1871 (2005).
24. Kuhn, M., Meiler, J. & Baker, D. Strand-loop-strand motifs: prediction of hairpins and diverging turns in proteins. *Proteins* 54, 282-288 (2004).
25. Bradley, P. & Baker, D. Improved beta-protein structure prediction by multilevel optimization of nonlocal strand pairings and local backbone conformation. *Proteins: Struct. Funct. Bioinf* 65, 922-929 (2006).
26. Altschul, S. F. et al. Gapped BLAST and PSI-BLAST: a new generation of protein database search programs. *Nucleic Acids Res.* 25, 3389-3402 (1997).
27. Camacho, C. et al. BLAST: architecture and applications. *BMC Bioinformatics* 10, 421 (2009).
28. Evangelidis, T. et al. Automated NMR resonance assignments and structure determination using a minimal set of 4D spectra. *Nat. Commun.* 9, 384 (2018).
29. Holm, L. & Laakso, L. M. Dali server update. *Nucleic Acids Res.* 44, W351-5 (2016).
30. Zimmermann, L. et al. A Completely Reimplemented MPI Bioinformatics Toolkit with a New HHpred Server at its Core. *J. Mol. Biol.* 430, 2237-2243 (2018).
31. Clark, P. Protein folding in the cell: reshaping the folding funnel. *Trends Biochem. Sci.* 29, 527-534 (2004).

Methods

Loop analysis. Loop connections between β-strands were collected from a non-redundant database of PDB structures obtained from the PISCES™ server[32] with sequence identity <30% and resolution ≤2 Å. We discarded those loops connecting β-strands with hydrogen bonded pairing (β-hairpins), and the remaining 5,061 β-arch loops were subsequently analyzed. The ABEGO torsion bins of each residue position were assigned based on the definition shown in FIG.

4, and the sidechain directionality pattern of neighboring residues was defined according to FIG. 1A. The secondary structure of all residue positions was assigned with DSSP and the last β-strand residue preceding and the first β-strand residue following the β-arch loop were chosen as the critical neighboring residues determining the sidechain pattern of the loop. The loop bending was defined as the angle between the loop center of mass and the two strand positions adjacent to the loop. Those loops with bending angles larger than 120 degrees were discarded from the analysis to correctly identify those loops producing a substantial change in the direction of the two connected β-strands.

Backbone generation. We used the Blueprint Builder™ mover of RosettaScripts™ to build protein backbones by Monte Carlo fragment assembly using 9- and 3-residue fragments compatible with the target secondary structure and torsion bins (ABEGO), as specified in the blueprints of every target topology. We used a poly-valine centroid representation of the protein and a scoring function accounting for backbone hydrogen bonding, Van der Waals interactions (namely to avoid steric clashes), planarity of the peptide bond (omega score term), and compacity of structures (radius of gyration). Thousands of independent folding trajectories are performed and subsequently filtered. Due to the non-local character of β-sheet contacts, we used distance and angle constraints to favor the correct hydrogen bonded pairing between β-strands main chain atoms. For every target topology we automatically set all pairs of residues involved in β-strand pairing to generate all constraints for backbone building. Protein backbones were filtered based on their match with the blueprint specifications (secondary structure, torsion bins and strand pairing), and subsequently ranked based on backbone hydrogen bonding energy (lr_hb score term), and the total energy obtained from one round of all-atom flexible-sequence design (see below)

Flexible sequence design. Generated protein backbones were subjected to flexible-sequence design calculations with RosettaDesign™ using the Rosetta™ all-atom energy function "Talaris2014" to favor amino acid identities and sidechain conformations with low-energy and tight packing. We performed cycles of fixed backbone design followed by backbone relaxation using the FastDesign mover of RosettaScripts™. Designed sequences were filtered based on total energy, sidechain packing (measured with RosettaHoles™, packstat and core side-chain average degree), sidechain-backbone hydrogen bond energy, and secondary structure prediction (match between the designed secondary structure and that predicted by Psipred based on the designed sequence). Amino acid identities were restricted based on the solvent accessibility of protein positions, ensuring that hydrophobic amino acids are located in the core and polars in the surface. Further restrictions were imposed to improve sequence-structure compatibility in loop regions. Sequence profiles were obtained for naturally occurring loops with the same ABEGO string sequence, as done previously[21].

For those blueprints that yielded the lowest energy designs we performed a second round with ten times more backbone samples. Backbones generated in this second round were subjected to more exhaustive sequence design by running multiple Generic Monte Carlo trajectories optimizing total energy and sidechain average degree simultaneously, and then applied all filters described above.

Design of disulfide bonds and helix capping domain. We used the Disulfidize mover of RosettaScripts™ to identify pairs of residue positions able to form disulfide bonds with a good scoring geometry. We searched for disulfide bonds between residues distant in primary sequence and with a disulfide score <−1.0. We designed a C-terminal helix capping domain (followed with a β-strand pairing with the first β-strand) using the backbone generation protocol described above but starting from design BH_6. The structure of BH_6 was kept fixed during fragment assembly and the C-terminal domain was generated. Then sequence design was performed for the C-terminal domain and those neighboring residues within 10 Å.

Sequence-structure compatibility. For assessing the local compatibility between designed sequences and structures we picked 200 naturally occurring fragments (9- and 3-mers) with sequences similar to the design and evaluated the structural similarity (by RMSD) between the ensemble of picked fragments and the local designed structure. Those with overall low RMSD fragments, and therefore with high fragment quality, were subsequently assessed by Rosetta™ folding simulations using the Rosetta™ energy function "ref2015". First, biased forward folding simulations (using the three-lowest RMSD fragments and 40 folding trajectories) were used to quickly identify those designs more likely to have funnel-shaped energy landscapes. Those designs achieving near-native sampling (RMSD to target structure below 1.5 Å) were then assessed by standard Rosetta™ ab initio structure prediction.

Figure 9:
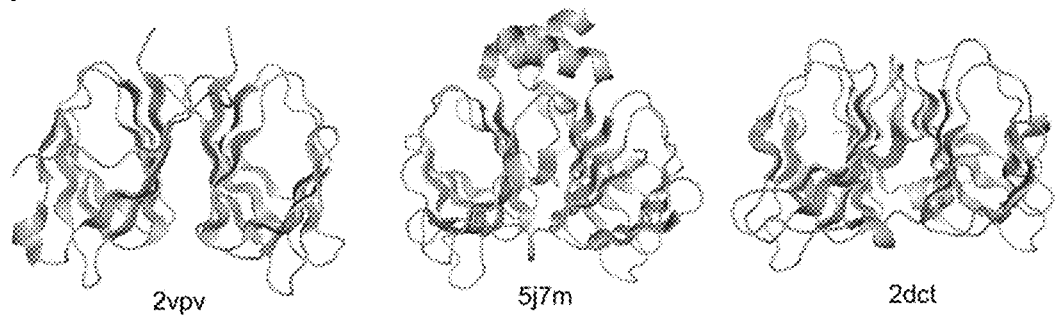
FIG. 9A-9B. Naturally occurring proteins with most similar structures or sequences to design BH_10. (A) Three closest structural analogs identified with DALI (Holm, L. & Laakso, L. M. Nucleic Acids Res. 44, W351-5, 2016) are homodimers. The sequence identity over structurally aligned regions ranged from 7 to 19%. (B) Three protein domains most similar in sequence and with structure available, as identified with HHpred (Zimmermann, L. et al. J. Mol. Biol. 430, 2237-2243, 2018), are also homodimers or part of a larger structure. For these three proteins the sequence identity with BH_10 was 21% and E-values ranged between 0.14 and 0.39. The natural proteins identified all exhibit more irregular secondary structures, longer loops and extra elements building protein interfaces.
Figure 9:
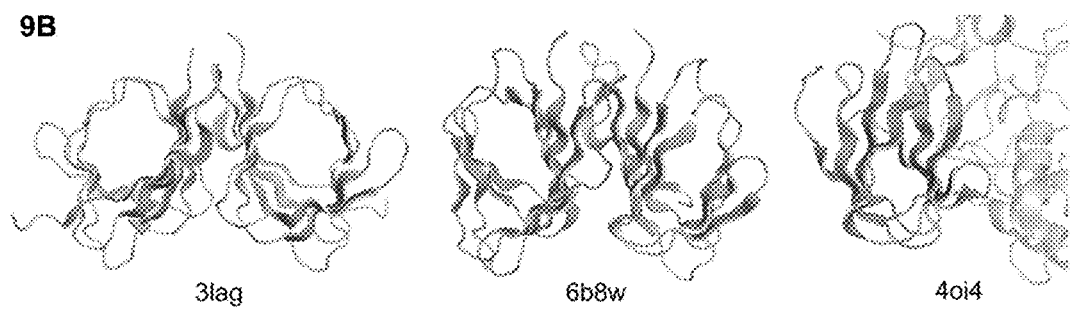

To evaluate the amount of β-hairpin sampling in each loop connection during ab initio structure prediction we first detected all strand pairings formed in each generated decoy and then mapped the residues involved in those strand pairings to the secondary structure elements of the designed structure. After secondary structure mapping, pairings between strands consecutive in the sequence were counted as β-hairpins. The total count of β-hairpins sampled in each loop over the total number of generated decoys is a relative quantity of hairpin sampling that allowed to compare the β-hairpin propensity of different loops and mutants, as shown in FIG. 9.

Contact order. To evaluate the non-local character of protein structures we computed contact order as the average sequence separation between pairs of Cα atoms within a distance of 8 Å and with a sequence separation of 3 residues at least.

Protein expression and purification. Genes encoding the designed sequences were obtained from Genscript and cloned into the pET-28b+ (with N-terminal 6×His tag and a thrombin cleavage site) expression vectors. Plasmids were transformed into *Escherichia coli* BL21 Star™ (DE3) competent cells, and starter cultures were grown at 37° C. in Luria-Bertani (LB) medium overnight with kanamycin. Overnight cultures were used to inoculate 500 ml of LB medium supplemented with antibiotic and cells were grown at 37° C. and 225 r.p.m until an optical density (OD600) of 0.5-0.7 was reached. Protein expression was induced with 1 mM of isopropyl β-D-thiogalactopyranoside (IPTG) at 18° C. and, after overnight expression, cells were collected by centrifugation (at 4° C. and 4400 r.p.m for 10 minutes) and resuspended in 25 ml of lysis buffer (20 mM imidazole and phosphate buffered saline, PBS). Resuspended cells were lysed in the presence of lysozyme, DNAse and protease inhibitors. Lysates were centrifuged at 4° C. and 18,000 r.p.m. for 30 minutes; and the supernatant was loaded to a nickel affinity gravity column pre-equilibrated in lysis buffer. The column was washed with three column volumes of PBS+30 mM imidazole and the purified protein was eluted with three column volumes of PBS+250 mM imidazole. The eluted protein solution was dialyzed against PBS buffer overnight. The expression of purified proteins was assessed by SDS-polyacrylamide gel electrophoresis and mass spectrometry; and protein concentrations were determined from the absorbance at 280 nm measured on a NanoDrop™ spectrophotometer (ThermoScientific) with extinction coefficients predicted from the amino acid sequences using the ProtParam™ tool. Proteins were further purified by FPLC size-exclusion chromatography using a Superdex™ 75 10/300 GL (GE Healthcare) column.

Circular dichroism (CD). Far-ultraviolet CD measurements were carried out with the AVIV 420 spectrometer. Wavelength scans were measured from 260 to 195 nm at temperatures between 25 and 95° C., using a 1 mm pathlength cuvette. Protein samples were prepared in PBS buffer (pH 7.4) at a concentration of 0.2-0.4 mg/mL.

Size exclusion chromatography combined with multiple angle light scattering (SEC-MALS). SEC-MALS experiments were performed using a Superdex™ 75 10/300 GL (GE Healthcare) column combined with a miniDAWN™ TREOS multi-angle static light scattering detector and an Optilab T-rEX™ refractometer (Wyatt Technology). One hundred microliter protein samples of 1-3 mg/ml were injected to the column equilibrated with PBS (pH 7.4) or TBS (pH 8.0) buffer at a flow rate of 0.5 ml/min. The collected data was analyzed with ASTRA™ software (Wyatt Technology) to estimate the molecular weight of the eluted species.

Protein expression of isotopically labeled proteins for structure determination. Plasmids were transformed using standard heat shock transformation into Lemo21 expression strain of $E.$ $coli$ (NEB) and plated onto a minimal M9 media containing glucose and kanamycin to maintain tight control over expression. A single colony was selected, inoculated into 50 mL of Luria Broth containing 50 ug/mL of kanamycin and grown at 37° C. with shaking overnight. After approximately 18 hours, the 50 mL starter culture was removed and 25 mL was used to inoculate 500 mL of Terrific Broth™ containing 50 ug/mL kanamycin and mixed mineral salts. The Terrific Broth™ (TB) culture was grown at 37° C. with shaking at 250 rpm until OD600 reached a value of 1.0. At this time the culture was removed and the cells were pelleted by centrifugation at 4000 rpm for 15 minutes. The TB broth was removed and the pelleted cells were resuspended gently with 50 mL of 20 mM NaPO4 150 mM NaCl pH 7.5. The resuspended cells were transferred into minimal labeling media, containing N15 labelled Ammonium Chloride at 50 mM and C13 glucose to 0.25% (w/v), as well as trace metals, 25 mM $Na_2HPO_4$, 25 mM $KH_2PO_4$, and 5 mM $Na_2SO_4$. The culture was returned to 37° C., at 250 rpm for 1 hour in order to replace unlabeled Nitrogen and Carbon with labelled Nitrogen and Carbon. After 1 hour, IPTG was added to 1 mM, the temperature was reduced to 25° C. and the culture allowed to express overnight. The following morning the culture was removed and the cells were pelleted by centrifugation at 4000 rpm for 15 minutes. The cells were resuspended with 40 mL of Lysis Buffer (20 mM Tris 250 mM NaCl 0.25% Chaps pH 8) and lysed with a Microfluidics M110P Microfluidizer at 18000 psi. The lysed cells were clarified using centrifugation at 24000×g for 30 minutes. The labelled protein in the soluble fraction was purified using Immobilized Metal Affinity Chromatography (IMAC) using standard methods (Qiagen Ni-NTA resin). The purified protein was then concentrated to 2 mL and purified by FPLC size-exclusion chromatography using a Superdex™ 75 10/300 GL (GE Healthcare) column into 20 mM NaPO4 150 mM NaCl pH 7.5. The efficiency of labelling was confirmed using mass spectrometry.

Visualization of protein structures and image rendering. Images of protein structures were created with PyMOL.

METHODS REFERENCES

32. Wang, G. & Dunbrack, R. L., Jr. PISCES: a protein sequence culling server. *Bioinformatics* 19, 1589-1591 (2003).
33. Kabsch, W. & Sander, C. Dictionary of protein secondary structure: pattern recognition of hydrogen-bonded and geometrical features. *Biopolymers* 22, 2577-2637 (1983).
34. Fleishman, S. J. et al. RosettaScripts: a scripting language interface to the Rosetta macromolecular modeling suite. *PLoS One* 6, e20161 (2011).
35. O'Meara, M. J. et al. Combined covalent-electrostatic model of hydrogen bonding improves structure prediction with Rosetta. *J. Chem. Theory Comput.* 11, 609-622 (2015).
36. Bhardwaj, G. et al. Accurate de novo design of hyperstable constrained peptides. *Nature* 538, 329-335(2016).
37. Sheffler, W. & Baker, D. RosettaHoles2: a volumetric packing measure for protein structure refinement and validation. *Protein Sci.* 19, 1991-1995 (2010).
38. Jones, D. T. Protein secondary structure prediction based on position-specific scoring matrices. *J Mol. Biol.* 292, 195-202 (1999).
39. Alford, R. F. et al. The Rosetta All-Atom Energy Function for Macromolecular Modeling and Design. *J Chem. Theory Comput.* 13, 3031-3048 (2017).
40. Studier, F. W. Protein production by auto-induction in high density shaking cultures. *Protein Expr. Purif.* 41, 207-234 (2005).
41. Delaglio, F. et al. NMRPipe: a multidimensional spectral processing system based on UNIX pipes. *J. Biomol. NMR* 6, 277-293 (1995).
42. Ying, J., Delaglio, F., Torchia, D. A. & Bax, A. Sparse multidimensional iterative lineshape-enhanced (SMILE) reconstruction of both non-uniformly sampled and conventional NMR data. *J. Biomol. NMR* 68, 101-118 (2017).
43. Lee, W., Tonelli, M. & Markley, J. L. NMRFAM-SPARKY: enhanced software for biomolecular NMR spectroscopy. *Bioinformatics* 31, 1325-1327 (2015).
44. Nerli, S., McShan, A. C. & Sgourakis, N. G. Chemical shift-based methods in NMR structure determination. *Prog. Nucl. Magn. Reson. Spectrosc.* 106-107, 1-25 (2018).
45. Lange, O. F. Automatic NOESY assignment in CS-RASREC-Rosetta. *J Biomol. NMR* 59, 147-159 (2014).
46. Lange, O. F. & Baker, D. Resolution-adapted recombination of structural features significantly improves sampling in restraint-guided structure calculation. *Proteins* 80, 884-895 (2012).
47. Berjanskii, M. V. & Wishart, D. S. Unraveling the meaning of chemical shifts in protein NMR. *Biochim. Biophys. Acta* 1865, 1564-1576 (2017).
48. Nilges, M. A calculation strategy for the structure determination of symmetric dimers by 1H NMR. *Proteins* 17, 297-309 (1993).
49. Nilges, M. Ambiguous distance data in the calculation of NMR structures. *Fold. Des.* 2, S53-7 (1997).
50. Herrmann, T., Gintert, P. & Withrich, K. Protein NMR structure determination with automated NOE assignment using the new software CANDID and the torsion angle dynamics algorithm DYANA. *J. Mo. Biol.* 319, 209-227 (2002).
51. Shen, Y. & Bax, A. Protein backbone and sidechain torsion angles predicted from NMR chemical shifts using artificial neural networks. *J. Biomol. NMR* 56, 227-241 (2013).
52. Chen, V. B. et al. MolProbity: all-atom structure validation for macromolecular crystallography. *Acta Crystallogr. D Biol. Crystallogr.* 66, 12-21 (2010).
53. Costantini, S., Colonna, G. & Facchiano, A. M. ESBRI: a web server for evaluating salt bridges in proteins. *Bioinformation* 3, 137-138 (2008).
54. *The PyMOL Molecular Graphics System*, Version 2.0 Schrödinger, LLC.

We claim:

1. A polypeptide comprising an amino acid sequence at least 90% identical to the amino acid sequence selected from the group consisting of SEQ ID NOS:1-24, wherein the polypeptide forms a beta-sheet.

2. The polypeptide of claim 1, wherein the polypeptide comprises two beta-sheets packing against each other forming a double-stranded beta-helix formed by 8 antiparallel beta-strands.

3. The polypeptide of claim 1, wherein the polypeptide comprises an amino acid sequence at least 90% identical to the amino acid sequence selected from the group consisting of SEQ ID NOS:10, 11, and 20-24.

4. The polypeptide of claim 1, wherein amino acid changes from the reference polypeptide do not include changes in proline residues present in loop connections between beta strands.

5. The polypeptide of claim 1, wherein amino acid changes from the reference polypeptide do not include changes in polar amino acid residues present in loop connections between beta strands capable of forming hydrogen bonds to the loop backbone.

6. The polypeptide of claim 5, wherein amino acid changes from the reference polypeptide do not include changes in hydrophobic amino acid residues present in the loop connections and adjacent to the polar amino acid residues between beta strands capable of forming hydrogen bonds to the loop backbone.

7. The polypeptide of claim 1, wherein amino acid changes from the reference polypeptide do not include changes in hydrophobic amino acid residues stabilizing the polypeptide core.

8. The polypeptide of claim 1, wherein amino acid changes from the reference polypeptide are conservative amino acid substitutions.

9. The polypeptide of claim 1 linked to a detectable label and/or immobilized on a surface.

10. The polypeptide of claim 1, comprising an amino acid sequence at least 95% identical to the amino acid sequence selected from the group consisting of SEQ ID NOS:1-24.

11. A scaffold, comprising the polypeptide of claim 1 bound to a metal, a ligand-binding molecule, or an enzyme active site.

* * * * *